United States Patent
Kosa et al.

(10) Patent No.: US 8,694,069 B1
(45) Date of Patent: Apr. 8, 2014

(54) FIBER-OPTIC PROBE WITH EMBEDDED PERIPHERAL SENSORS FOR IN-SITU CONTINUOUS MONITORING

(75) Inventors: Nadhir Kosa, The Woodlands, TX (US); Raghuvir Singh, The Woodlands, TX (US)

(73) Assignee: Kosense, LLC, The Woodlands, TX (US)

(*) Notice: Subject to any disclaimer, the term of this patent is extended or adjusted under 35 U.S.C. 154(b) by 522 days.

(21) Appl. No.: 12/972,628

(22) Filed: Dec. 20, 2010

Related U.S. Application Data

(60) Provisional application No. 61/284,536, filed on Dec. 21, 2009.

(51) Int. Cl.
*A61B 5/1455* (2006.01)
*G02B 6/00* (2006.01)

(52) U.S. Cl.
USPC ......................... 600/342; 264/1.24

(58) Field of Classification Search
USPC .................. 600/310, 322, 341, 342; 264/1.24
See application file for complete search history.

(56) References Cited

U.S. PATENT DOCUMENTS

| | | | |
|---|---|---|---|
| 4,200,110 A | 4/1980 | Peterson et al. | 128/2 |
| 4,476,870 A | 10/1984 | Peterson et al. | 128/633 |
| 4,558,014 A | 12/1985 | Hirschfeld et al. | |
| 4,682,895 A | 7/1987 | Costello | 356/39 |
| 4,752,115 A | 6/1988 | Murray, Jr. et al. | 250/257 |
| 4,758,814 A | 7/1988 | Howng et al. | 332/22 |
| 4,824,789 A | 4/1989 | Yafuso et al. | 422/58 |
| 4,849,172 A | 7/1989 | Yafuso et al. | 422/155 |
| 4,857,273 A | 8/1989 | Stewart | 436/805 |
| 4,861,727 A | 8/1989 | Hauenstein et al. | 250/277 |
| 4,889,407 A * | 12/1989 | Markle et al. | 385/12 |
| 4,974,929 A | 12/1990 | Curry | 350/96 |
| 5,005,576 A * | 4/1991 | Gunther | 600/311 |
| 5,006,314 A | 4/1991 | Gourley et al. | 422/82 |

(Continued)

FOREIGN PATENT DOCUMENTS

WO   WO 94/10553   5/1994

OTHER PUBLICATIONS

Walt, Fiber-optic sensors for continuous clinical monitoring, Proc. of IEEE, v. 80, Jun. 1992.

(Continued)

*Primary Examiner* — Eric Winakur
(74) *Attorney, Agent, or Firm* — Yakov Sidorin; Quarles & Brady LLP

(57) ABSTRACT

A fiber-optic (FO) element-based sensing probe for use in monitoring parameters of a biological environment. A straight FO-element, embedded and cast in a polymeric body of the probe delivers excitation light from a light source on one side of the FO-element to a chamber, inside the body, that is filled with an indicator matrix responsive to the excitation light and to the presence of a biological environment. The same straight FO-element collects light from the chamber and delivers it, in an opposite direction, from the chamber to an optical detector. The chamber may be configured to be co-axial with the FO-element and to have a transverse dimension, across the axis of the FO-element, exceeding the outer diameter of the core of the FO-element. A membrane permeable to an analyte of the biological environment is disposed in a recess of the chamber adjoining the aperture defined by the chamber in an outer side surface of the polymeric body.

18 Claims, 12 Drawing Sheets

(56) References Cited

U.S. PATENT DOCUMENTS

| | | | |
|---|---|---|---|
| 5,012,809 A | 5/1991 | Shulze | 128/633 |
| 5,018,529 A | 5/1991 | Tenerz | 128/672 |
| 5,047,208 A | 9/1991 | Scweitzer et al. | |
| 5,124,130 A | 6/1992 | Costello et al. | 422/82 |
| 5,127,405 A | 7/1992 | Alcala et al. | 128/633 |
| 5,335,305 A | 8/1994 | Kosa et al. | 385/59 |
| 5,397,411 A | 3/1995 | Costello et al. | 264/1 |
| 5,408,999 A | 4/1995 | Singh et al. | 128/633 |
| 5,830,138 A | 11/1998 | Wilson | 600/325 |
| 6,256,522 B1 | 7/2001 | Schultz | 728/633 |
| 6,303,386 B2 | 10/2001 | Klimant | 422/82 |
| 6,531,097 B1 | 3/2003 | Vojnovic et al. | 422/55 |
| 6,599,746 B1 | 7/2003 | Gumbrecht | 436/8 |
| 6,890,307 B2 * | 5/2005 | Kokate et al. | 600/549 |
| 7,209,605 B2 | 4/2007 | Cantin | 385/12 |
| 2008/0199360 A1 | 8/2008 | Shahriari | |
| 2009/0075321 A1 | 3/2009 | Obeid et al. | |
| 2009/0216097 A1 | 8/2009 | Wilson et al. | |

OTHER PUBLICATIONS

Mignani et al., Biomedical sensors using optical fibers, Rep. Prog. Phys., v. 59, pp. 1-28, 1996.

Murkovic et al., Sensors in neonatal monitoring: Current practice and future trends, Technology and Health Care, v. 11, pp. 399-412, 2003.

Peura, Chemical Biosensors, Chapter 10, in "Medical Instrumentation Application and Design", 4th Edition, (Editor: John G. Webster, John Wiley & Sons, Inc., 2009).

Seitz, Chemical Sensors Based on Fiber Optics, Report, Analytical Chemistry, v. 56, No. 1, Jan. 1984.

* cited by examiner

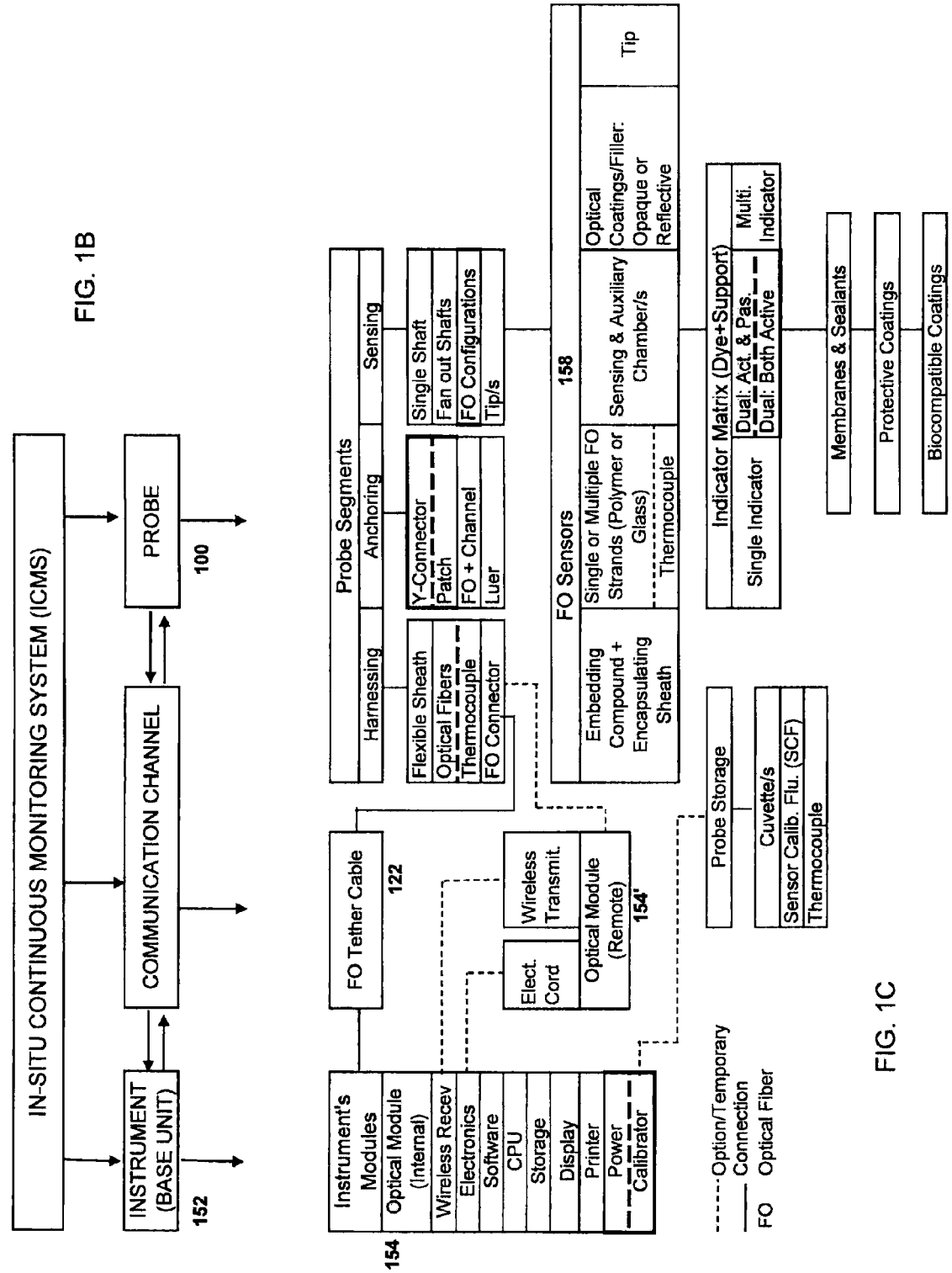

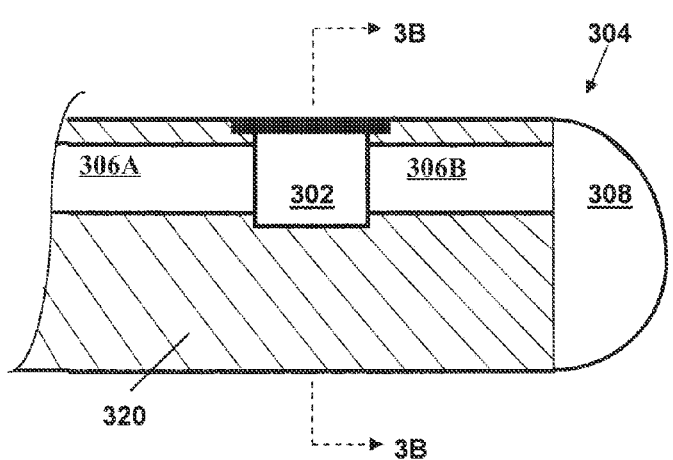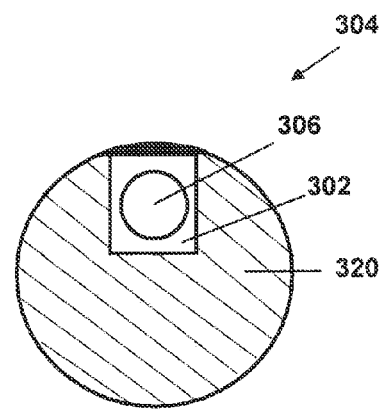
FIG. 3A  FIG. 3B
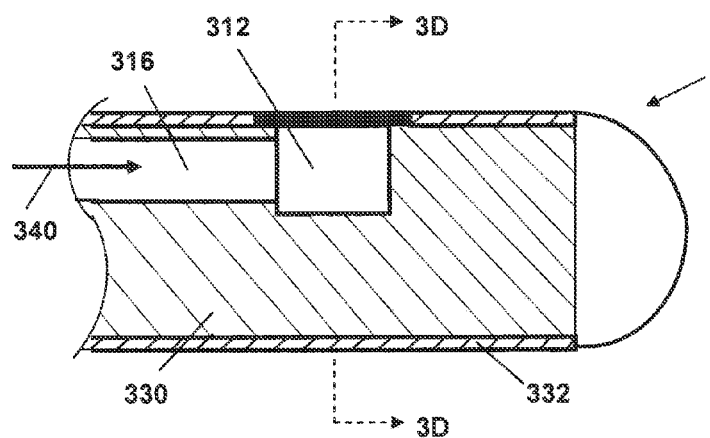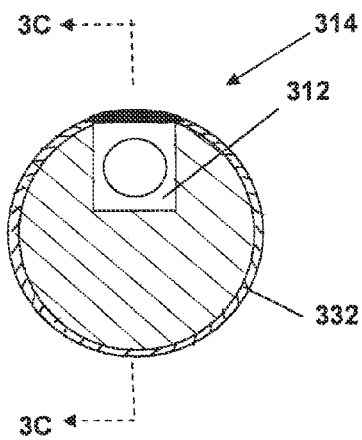
FIG. 3C  FIG. 3D

FIBER-OPTIC PROBE WITH EMBEDDED PERIPHERAL SENSORS FOR IN-SITU CONTINUOUS MONITORING

CROSS REFERENCE TO RELATED APPLICATIONS

This application claims the benefit of and priority from U.S. Provisional Patent Application No. 61/284,536 filed on Dec. 21, 2009 and titled "Indicator-based fiber optic probes for sensing various parameters," the disclosure of which is hereby incorporated by reference in its entirety.

TECHNICAL FIELD

The present invention relates to sensing probes employing fiber optic sensors and, more particularly, to sensing probes that include multiple embedded peripheral sensors employing for monitoring of physiological parameters of patients (e.g., critically-ill patients) in a clinical setting.

BACKGROUND ART

The field of fiber optic (FO) sensors has been subject of extensive research and development and applications of such sensors cover a broad range of parameter measurements such as measurements of physical, biomedical, chemical, biochemical and physiological parameters such as, for example, measurements of oxygen, pH, or carbon dioxide concentration in blood, or measurement of blood glucose and lactate. In comparison, the related art is relatively silent with respect to FO-sensors adapted to measure such blood electrolytes as sodium, potassium, calcium, and chloride, among others. Possible reasons for limited teachings in this area include the fact that the real-time adjustment of levels of these electrolytes in the ill-patient's blood is not as critical to the patient's health management as the real-time adjustment of levels of oxygen, pH, or $CO_2$, for example. as a result, it often suffices to monitor these electrolytes intermittently and not continuously.

FO-optical sensors of the related art (such as, for example, U.S. Pat. Nos. 4,682,895; 5,006,314; 4,974,929; 4,824,789) conventionally include an indicator (dye) such as fluorescent or absorption dye, which interacts with the component to be sensed or measured. Fluorescent dyes, the emissions of which, produced under illumination by light delivered through an optical fiber from an optical source, are affected by the blood constituents or analytes are often incorporated in a semi-permeable polymeric matrix and attached to the optical fiber. The intensity of such fluorescence of the dye relates to the level of an analyte in a sample under test, and therefore can be collected, delivered to a detector, and measured to give an indication of the concentration of the blood constituent. FO-based sensing probes of the related art may include a reflection-based optical path or a fluoremetric indicator system. Discussion of the related art and applications can be also found in "Chemical Sensors Based On Immobilized Indicators And Fiber Optics," by W. Rudolf Seitz from *Fiber Optic Chemical and Biosensors* (Otto S. Wolfbeis, vol. I & II, CRC Press, 1991, Boca Raton, Fla., 1991), or "*Principles of Fluorescence Spectroscopy*" by Joseph R. Lakowicz (Springer, New York, 2006) and "*Biomedical Sensors Using Optical Fibers*," A. G. Mignani and F. Balidini, Rep. Prog. Phys., v. 59, 1-28 (1996) and other publications. Various related patents include, to name just a few, U.S. Pat. Nos. 5,124,130; 5,397,411; 5,335,305, and 5,408,999 and the PCT Publication WO 94/10553 disclosing methods and chemical compositions related to a tri-analyte FO biocompatible probe for use in critical care environment. U.S. Pat. No. 4,849,172 disclosing an optical sensor having a gas permeable silicone matrix that contains a high concentration of an optical indicator consisting essentially of a mixture of derivatives of a polynuclear aromatic compound and U.S. Pat. No. 4,857,273 disclosing a sensor including a means for enhancement of a light signal; a U.S. Pat. No. 4,861,727 describing a luminescent oxygen sensor using a lanthanide complex; a U.S. Pat. No. 4,558,014 disclosing an assay apparatus employing fluorescence effects; and U.S. Patent Application Publication No. 2008/0199360 teaching methods of making fluorescence oxygen sensor based on sol-gel materials incorporating fluorescent dyes in such a relatively unstable fashion allowing the dyes to be washed out over time the sensor is being exploited. The use of sensors discussed in these patent documents is restricted to non-clinical applications where size or biocompatibility issues are not critical.

One of the known applications of FO-sensors related to survival of tissue cells, which rely on adequate supply of oxygen to the mitochondria within the tissue cells. The significance of partial pressure of brain tissue oxygen measurements demonstrating cerebral hypoxia, ischemia, or both is very well known. For example, continuous brain-tissue monitoring involving measurements of oxygen delivery and identification of cerebral hypoxia and ischemia in patients with brain injury, aneurysmal subarachnoid hemorrhage, malignant stroke, or other patients at risk for secondary brain injury has been described in related art employing Fiber Optic-sensors the operation of which is based on measurements of either intensity or life-time decay of generated fluorescent light. The decay life-time of fluorescence, for example, is inversely proportional to the concentration of oxygen and relates to an absolute value of $pO_2$ in mm Hg. U.S. Patent Application Publication No. 2009/0075321 discloses a fiber optic sensor for measuring oxygen concentration in tissue and comprising an optical glass fiber passing through a gas-isolation collar into a cavity filled with a polymer and a fluorescent dye material. Fluorescent indicator material used in this invention uses platinum complex of substituted porphyrines. A related configuration using a phosphorescent based solution, encapsulated with an oxygen permeable membrane, which produces oxygen-quenchable phosphorescence, is reported in U.S. Patent Application Publication No. 2009/0216097. An example of a fluoremetric fiber optic sensor is described in U.S. Patent Application Publication No. 2009/0075321, discussing the employment of optical fiber extending longitudinally into an elongated cavity that is defined by a surrounding wall and has an open end remote from that through which the optical fiber passes. Each of the above mentioned patent documents is incorporated herein by reference in its entirety.

Shortcomings of conventional fiber-optic based biological sensors prevent the existing designs from assuring the optimized operation in field conditions. Three common types of design are representative in this respect. For example, the use of bent upon itself fiber optic (for example, looped over a mandrel or spoke, with radius comparable to that of the optical fiber), the input and output segments of which are both contained within the body of the probe not only significantly decreases the efficiency of light transmission due to light leaks at a tight-radius bend but also sets a low limit on the density of FO-elements within the probe. The use of shallow cavities, in the fiber optic, that graze the fiber optic core limit the degree of interaction between the excitation light and the analyte and thus does not allow to increase the sensor's sensitivity above a certain level. Yet in another common implementation, the placement of the analyte-sensitive material adjacent to the tip of the fiber optic that is being inserted into a biological tissue makes the sensing probe vulnerable to being disrupted and mechanically disintegrated.

It is an aim of fiber optic sensor/probe development to combine more than one sensor in a single probe so that a patient is not overtaxed with various probes introduced in his or her arteries or skin tissues. While the related literature offers a variety of designs attempting to achieve this goal, the problem is far from being solved and there remains a need in a multi-sensor probe having an optimized density of fiber-optic sensors that perform continuous, real-time, and temperature and pressure-normalized determination of physiological elements such as analytes and/or physical parameters describing a biological environment (such as a patient under test) and that have optimized sensitivity. The present invention addresses the operational shortcoming of the related art and offers a probe having optimized density of fiber-optic sensors.

SUMMARY OF THE INVENTION

An embodiment of the present invention provides a fiber-optic (FO) probe that includes an elongated body having proximal and distal ends, a side surface, a peripheral portion and an axis. The embodiment also includes a straight optical communication channel extending along and cast inside the peripheral portion of the elongated body between the proximal and distal ends and a chamber inside the elongated body. The chamber has a wall and defines an aperture in the side surface and may have a transverse extent exceeding that of the optical communication channel, while the optical communication channel is configured to transmit light between the proximal end and the chamber and has an end-facet at the wall.

Inside the chamber there is an indicator material disposed in the chamber, optionally in physical contact with the end-facet of the optical communication channel. The indicator material is adapted, when illuminated with excitation light, to either generate fluorescent light or to change the level of intensity of the excitation light that has passed through the indicator material. The elongated body may additionally include a central optical communication channel axially cast or embedded within the elongated body and configured as a temperature sensor. In a specific embodiment, the optical communication channel includes a first FO-element cast inside the elongated body and configured such that a field-of-view (FOV) associated with a numerical aperture (NA) of the first FO-element is contained within the chamber and the chamber has a transverse extent exceeding the outer diameter of the first FO-element. the first FO-element is configured to deliver excitation light to the indicator material inside the chamber and to collect response light generated by the indicator material.

The optical communication channel of the embodiment may additionally include a second FO-element cast inside the elongated body and having a second end-facet at a chamber wall such that the first and second FO-elements are co-axial and are spatially separated by the chamber. At least one of the first and second FO-elements may be disposed within a color-coded tube or, in a specific case, within an opaque tube, and the indicator material may be in physical contact with at least one of the first and second end-facets. Further more, the embodiment may include a membrane patch disposed within a recess of the chamber and configured to enable fluid communication between the indicator material and the ambient medium. Such a patch may be overcoated, on its outer surface, with a thin-film layer that enhances at least one of anti-thrombogenic, mechanical, hydrophilic, and optical characteristics of the FO-probe. Moreover, the wall of the cavity may carry a thin-film coating configured to enhance at least one of reflection and absorption of light inside the chamber.

An embodiment of the FO-probe as described above may be configured as part of an in-situ continuous monitoring system (ICMS) that also includes (i) a base unit operably connected to the first FO-element, the base unit including at least one of a light source, an optical detector, an optical filter, and a mechanical alignment mechanism; and (ii) a harnessing portion adapted to enclose the first FO-element and to connect the base unit and the elongated body. The embodiment of an ICMS may further include an anchoring portion including a connector encapsulating the proximal end and a rotatable lure, wherein the first FO-element passes through the anchoring portion towards the base unit.

Another embodiment of the invention provides a method for operating a fiber-optic (FO) sensor of an in situ continuous monitoring system (ICMS) including an elongated body having a side surface, the method comprising the steps of (a) transmitting light from a light source of the ICMS through an optical system having a numerical aperture (NA) to a field-of-view (FOV) associated with the NA inside a chamber of the ICMS, the chamber being filled with an indicator material and having a wall and an opening that enables fluid communication between the indicator material and an analyte outside of the side surface-, wherein the optical system includes a first optical communication channel having a first end-facet at the wall; (b) exciting, with the transmitted light, the indicator material that has interacted with the analyte through the opening thereby causing the indicator material to generate response light having optical characteristics representative of the analyte; and (c) capturing, by the optical system within the NA, at least a portion of the response light. The optical system of the method is at least partially embedded in a material from which a portion of the ICMS is made, and the first optical communication channel includes a first straight FO element embedded in a peripheral portion of the elongated body in physical contact with the indicator material. In a specific embodiment of the method, the chamber has a transverse cross-section with extent exceeding that of the first end-facet.

The embodiment of the method may additionally include the steps of delivering the response light, through the optical system, to an optical detection unit of the ICMS; and processing, in a computer processor of the ICMS, the data associated with the delivered response light to identify characteristics of the analyte. Both the transmission of light from the light source to a FOV and the delivering of the response light to an optical detection unit occurs through the same fiber optic FO-element embedded in a peripheral portion of the elongated body, and the transmitting light from a light source of the ICMS through an optical system includes transmitting light through a central fiber optic FO-element axially embedded within the elongated body towards a second chamber axially disposed at an end of the central FO-element, the central FO-element being configured as a temperature sensor.

In addition, the method may include a step of re-circulating the transmitted light inside the chamber, wherein the transmitted light traverses the indicator material more than once.

Yet another embodiment of the invention provides an in situ continuous monitoring system (ICMS) employing a fiber-optic (FO) probe having at least one analyte-selective FO-sensor cast in a peripheral portion of the probe and a central temperature sensor axially cast within the probe, the ICMS comprising an optical module including a light source and a light detector; a computer processor configured to process data representative of at least light intensity; and a calibration jig configured to enable calibration of the FO-probe with respect to at least two analyte-selective references. An embodiment of the ICMS may further comprise a tangible computer-readable storage medium configured to store data representative of at least light intensity and calibration data. In one implementation of the ICMS, the employed FO-probe includes a sensing portion configured for insertion into a biological tissue, the sensing portion having an axially disposed chamber that is in contact with a FO-element of the central temperature sensor and a tip covering the axially disposed chamber, the axially disposed chamber having transverse dimensions exceeding those of the FO-element of the central temperature sensor.

An additional embodiment provides a method for fabrication of a fiber-optic (FO) probe, for monitoring a physiological element of a biological tissue, the FO probe including at least one straight FO-element extending between a proximal end of the probe and a distal end of the probe, each FO-element terminating at a surface inside an elongated body of the FO probe, the method including the steps of (a) embedding the at least one pre-aligned straight FO-element with a polymeric compound within a predetermined spatial extent; (b) curing the polymeric compound thereby forming the elongated body within said spatial extent, the elongated body including the at least one FO-element cast in a peripheral portion of the body; (c) defining an aperture in an outer side surface of the elongated body and carving out, through this aperture, an inner portion of the body so as to form the surface inside the body, wherein an end-facet of the FO-element defines the surface; and (d) disposing an indicator-matrix inside the body and adjacent to the end-facet of the FO-element. the FO-element is configured to deliver light from the proximal end to the indicator-matrix, to collect light from the indicator-matrix, and to deliver the collected light to the proximal end.

Moreover, the embodiment may also include a step of placing a patch in the aperture and, in particular, in a recess that has been defined, in the proximity of the aperture, by the surface inside the body. A specific patch may be permeable to the physiological element. The carving out may include removing a fragment of the cast and FO-element so as to interrupt the continuity of the FO-element to form discrete FO-sub-elements and wherein the surface extends into the body beyond the end-facet of the FO-element. The surface may carry at least one thin-film coating configured to change characteristics of light impinging upon the surface.

The method for fabricating the FO-probe may additionally include coating the outer side surface of the body with at least one thin-film coating enhancing at least one of optical characteristic, anti-thrombogenic (AT) characteristic, anti-viral (AV) characteristic, and anti-inflammatory (AI) characteristic of the probe and/or forming a non-traumatizing tip at the distal end.

Yet another embodiment of the invention provides for a fiber-optic (FO) probe that includes (i) an elongated body having an axis, proximal and distal ends, a side surface, and a chamber inside the body, the chamber having a wall and an opening through the side surface; (ii) a straight optical communication channel extending along and cast inside the elongated body between the proximal and distal ends, the straight optical communication channel having an end-facet at the wall, the straight optical communication channel configured to transmit excitation light launched through the proximal end through the end-facet into the chamber; and (iii) an indicator material disposed inside the chamber and adjoining the end-facet, the indicator material adapted to generate response light in response to being illuminated with the excitation light, the indicator material having optical characteristics that are dependent on a presence of an analyte, wherein an extent of the chamber transverse to the axis exceeds a transverse extent of the straight optical communication channel and wherein the straight optical communication channel is configured to collect the response light and deliver it from the end-facet towards the proximal end. The wall of the embodiment may contain a recess adjacent to the opening. Moreover, the embodiment may contain a membrane disposed in the opening and permeable to the analyte.

Such embodiment of an FO-probe may be configured as part of a measurement system that includes an optical module containing a light source and a light detector; a computer processor configured to process data representative of at least light intensity; and a calibration jig adapted to enable the calibration of the FO-probe with respect to at least two analyte-selective references.

BRIEF DESCRIPTION OF THE DRAWINGS

The invention will be more fully understood by referring to the following Detailed Description of Specific Embodiments in conjunction with the Drawings, of which:

FIG. 1B shows an embodiment of an in situ continuous monitoring system containing an embodiment of the sensing probe such as that of FIG. 1A.

FIG. 1C is a diagram providing details of the embodiment of FIG. 1B.

FIGS. 2(A, B) show an embodiment of the sensing portion of the probe.

FIGS. 3(A, B) schematically illustrate, in side and cross-sectional views, another embodiment of the sensing portion of the probe having a sensor with an in-line chamber.

FIG. 3(C, D) schematically illustrate, in side and cross-sectional views, another embodiment of the sensing portion of the probe having sensor with an end-line chamber.

DETAILED DESCRIPTION OF SPECIFIC EMBODIMENTS

Figure 1A:
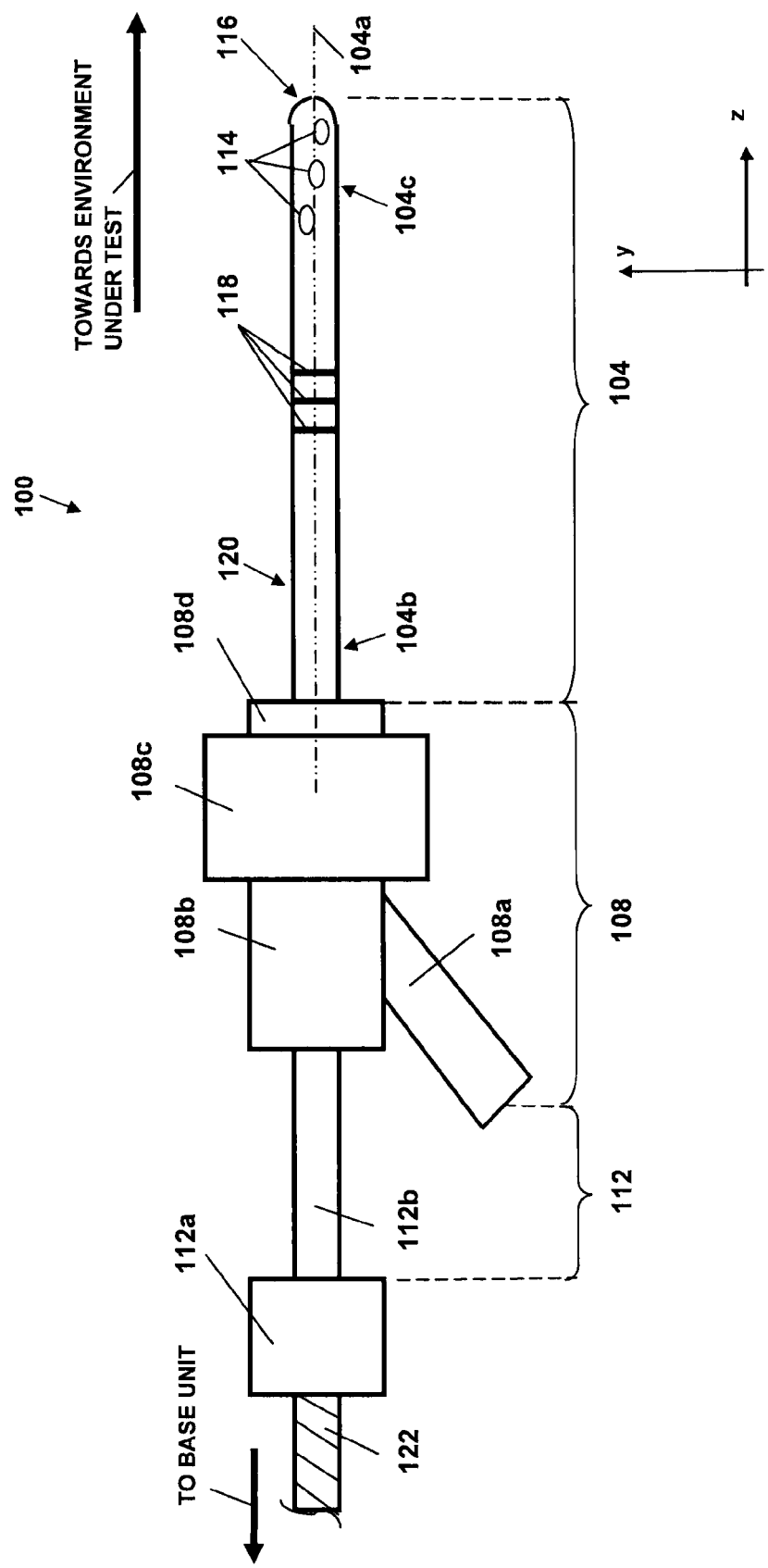
FIG. 1A is an embodiment of a sensing probe of the invention including a sensing portion, an anchoring portion, and a harnessing portion.

The following specification provides a description of the embodiments of the invention with reference to the accompanying drawings. In the drawings, wherever possible, the same reference numerals and labels refer to the same or like components or elements. It will be understood, however, that similar components or elements may also be referred to with different numerals and labels.

Throughout this specification, a reference to "one embodiment," "an embodiment," or similar language implies that a particular feature, structure, or characteristic described in connection with the embodiment referred to is included in at least one embodiment of the present invention. Thus, phrases "in one embodiment," "in an embodiment," and similar terms used throughout this specification may, but do not necessarily, all refer to the same embodiment. Moreover, it will be understood that features, elements, components, structures, details, or characteristics of various embodiments of the invention described in the specification may be combined in any suitable manner in one or more embodiments. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention.

If the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

DEFINITIONS

As used in this description and the accompanying claims, the following terms shall have the meanings indicated, unless the context requires otherwise:

An "analyte" is a substance or chemical constituent that is determined in an analytical procedure such as, for example, a chemical or a biochemical measurement conducted with the use of biochemical sensors. For instance, in blood testing, depending on the type of testing, an analyte may be oxygen, pH, glucose, lactate, sodium, potassium, calcium or other blood electrolytes.

A term "indicator-matrix" generally refers to a material facilitating a determination of presence and, possibly, characteristics of an analyte in the analytical procedure of choice. Typically, an indicator-matrix includes an indicator (a chemical composition or substance that actively reacts to the presence of the analyte by changing at least some of its physical characteristics) hosted in a supporting material sometimes referred to as substrate. An example of an indicator-matrix is provided by a combination of a dye, whether fluorescent or absorptive, supported in a glass-like material such as sol-gel, that interacts with the analyte to be measured and that, in response to such interaction, changes its optical properties. An indicator-matrix including a fluorescent dye, for example, in response to being illuminated with appropriate incident light generates fluorescent light at least one characteristic (for example, intensity) of which depends on interacting of the fluorescent dye with a particular analyte.

An optical waveguide (interchangeably referred to herein as a waveguide) is a term generally reserved, for the purposes of this disclosure, for an optical system such as one having an elongated structure used to guide light longitudinally by confining such light in two transverse dimensions. One example of a waveguide employed by embodiments of the invention is a fiber-optic (FO) element that includes at least one optical fiber, whether single- or multi-mode and whether made of glass or plastic. In some embodiments, a light-pipe, or a bundle of optical fibers may be used.

A probe (which may also be interchangeably referred to herein as a sensing probe) is a sub-system that embeds, within at least one of its components refereed to as a sensing portion of the probe, at least one optical waveguide and a chamber filled with an indicator-matrix configured in optical communication with the waveguide. The indicator-matrix of the probe may be in fluid communication with a medium surrounding the probe, in which case the probe also includes a selective membrane separating the indicator-matrix from the outside (or ambient) medium. In operation, the indicator-matrix is at least partially exposed through the selective membrane to the ambient medium, the detection and/or measurement of the physiological parameters of which is thus enabled in-situ through interaction between the analyte and the indicator. A probe may additionally accommodate elements adapted to sense physical parameters of the ambient such as, for example, temperature and pressure. The at least one optical waveguide element (and, optionally, an FO-element-based pressure-sensor element) of the probe are preferably disposed in a peripheral portion of the embedding component of the probe. In order not to overtax the peripheral portion, a temperature-sensing element (configured on the basis of either a FO-element or a thermocouple) is optionally placed in a central, axial portion of the embedding body and capped with a thermally-conductive material to allow for either proper thermal calibration of other sensors, the operation of which is temperature-sensitive, or for independent temperature measurement. The sensing probe may be configured as part of a larger photonic-based continuous monitoring system, which includes additional components and devices such as a light source, a detector, electronic circuitry, a computer system including but not limited to tangible computer-readable storage medium and an optical display, and mechanical components and elements of a housing structure that facilitate the operation of the probe and the collection and processing of data indicative of characteristics of the analyte and the measured physical parameters of the ambient.

The scope of a term "fluid" covers both liquid and gas substances. Consequently, "fluid communication" implies a connection providing for exchange or transportation of either liquid or gas through a predetermined boundary or a pre-defined spatial limit. In reference to a membrane that is permeable to fluid and that separated one space region from another, the mentioned space regions are understood to be in fluid communication with one another if either liquid or gas can penetrate through the membrane from the first spatial region to the second spatial region.

Similarly, a term optical communication implies an optical means of access. For example, when point A and point B are said to be in optical communication with one another, it means that light energy present at point A can propagate to point B, and vice versa.

As broadly used and described herein, the reference to a layer or coating as being "carried" on a surface of an element refers to both a layer that is disposed directly on the surface of an element or a layer that is disposed on another coating, layer or layers that are, in turn, disposed directly on the surface of the element.

The idea of the present invention stems from the realization that the optimization of a degree of interaction of light illuminating an indicator-matrix with the indicator component of the indicator-matrix, in an analytical procedure conducted with the use of a waveguide-based probe, may be achieved and adjusted, as required by a given application, through configuring the employed waveguide and an indicator-matrix in a specific, technologically subtle fashion that thus far remained imperceptible to and undefined by a skilled artisan. Specifically, on one hand, the indicator-matrix should preferably be configured to have a volume that interacts not with evanescent, leaking, or radiation fields of the optical waveguide but with light corresponding to a transverse guided mode, which contains most of guided-light energy and which is referred to herein as excitation light. On the other hand, the volume of the indicator-matrix and its orientation with respect to the waveguide delivering the excitation light to it should preferably be configured to have such longitudinal and transverse extents, with respect to excitation light, as to optimize the overlap between the excitation light and the volume and thus optimize the generation of fluorescent light in the indicator-matrix.

Moreover, the probe should employ a waveguide or a system of waveguides each of which is devoid of bends and signals transmission interruptions and is substantially straight, thereby reducing the amount of optical losses in the waveguide and increasing the amount of the excitation light and, therefore, the general sensitivity of the probe to changes occurring in the indicator upon its interaction with the ambient medium. Employing only straight FO-elements in the probe additionally facilitates miniaturization of the instrument, and allows to increase the number of FO-element-based sensors per unit cross-sectional area of the probe. By way of example, in a FO-based probe of the related art that includes more than one FO-element disposed in proximity of one another, the component FO-elements have to be spaced apart anywhere along their lengths by some minimal threshold distance. Indeed, when the separation distance is below a determinable threshold value, the leakage of light occurring at bends of adjacent FO-elements of a related-art sensors, or outcoupling of light at facets of the adjacent FO-elements where at least one indicator-matrix is disposed (according to the teachings of the related art), causes an optical cross-talk between the individual sensors. The latter inevitably reduces the quality of the performance of the sensor. Implementations of the idea of the present invention eliminate this requirement imposing a limit on spatial separation between the component FO-elements in a probe, thereby affording higher packing density on sensors in a given probe and/or reducing the cross-sectional size of the probe containing a predetermined number of sensors. In particular, the maximum number of FO-element-based sensors that can be accommodated by an embodiment of the probe is determined by the ratio of the outer diameter (OD) of the structure of the probe to that of an optical fiber employed by the probe.

Furthermore, improving longevity and mechanical stability of the indicator material according to the present idea includes a disposition of the indicator material away from a tip of the probe, which, unlike the conventional placement of an indicator-matrix at the tip of the fiber-optic strand of a FO-based sensor of the related art, does not result in exposure and susceptibility of the indicator material to external impacts and damage during exploitation. The conventional disposition of the indicator-matrix at a tip of the fiber-optic strand has an additional shortcoming as the amount and orientation of an indicator-matrix so placed with respect to the fiber-optic strand is difficult to control during the fabrication of the sensing probe.

The idea of the present invention also stems from the realization that a degree to which the generated fluorescent light can be captured by the waveguide can also be optimized using similar considerations and that optimization is achieved with the use of the same straight waveguide for both the delivery of the excitation light to the indicator-matrix and the collection of the resulting fluorescent light.

In accordance with an exemplary embodiment, described with reference to FIG. 1A, an embodiment 100 of the sensing probe of the invention is illustrated schematically. The embodiment 100 is shown to include three portions: a sensing portion 104, an anchoring portion 108, and a harnessing portion 112. As discussed in further detail below, the sensing portion 104 has a longitudinal axis 104a and embeds at least one waveguide such as a FO-element (not shown) molded or cast in the sensing portion 104 to linearly extend, without bends, from a proximal end 104b of the sensing portion 104 towards its distal end 104c, and at least one respective indicator-matrix (not shown) disposed within at least one corresponding chamber 114 in optical communication with the FO-element to enable a FO-based analyte sensor. The sensing portion 104 may further contain a physical-parameter sensor (not shown) such as a temperature sensor and/or a pressure sensor. It is appreciated that, while analyte sensors and physical-parameter sensors of an embodiment are preferably disposed in a peripheral part, as seen in a transverse cross-section, of the distal end 104c of the sensing portion 104, the temperature sensor is optionally molded or cast in the central portion of the distal end 104c so as to optimize temperature sensing and enable accurate temperature calibration of the analyte sensors. The middle part and the proximal end 104b of the sensing portion 104 include the extensions of the FO-elements that are enclosed into a thin-walled tube, which structurally supports the FO-elements but not necessarily aligns them with respect to one another. The thin-walled tube extends towards the anchoring portion 108. Positions of the FO-elements' extensions inside this thin-walled tube are not critical for the operation of the embodiment and, in practice, the proximal end 104b with the extensions of the FO-elements may have any predetermined length and configuration such as, for example, straight or curved, stiff or flexible.

Each of the FO-element-based analyte sensor(s) and any physical-parameter sensor present in an embodiment are extended through the anchoring portion 108 and the harnessing portion 112 and further through an optional connector 112a towards a base unit (not shown) that incorporates photonic, mechanical, and computer sub-systems facilitating the operation of the embodiment 100. As discussed in more detailed elsewhere in this application, the sensing portion 104 may be equipped with membrane components and auxiliary optical and biological coatings.

In operation, the sensing portion 104 is at least partially inserted into a biological environment or medium the parameters of which are being measured with the embodiment 100. For example, the sensing portion 104 may be inserted into a living tissue subcutaneously or, alternatively, into a blood vessel such as an artery, or the brain, or a bodily cavity to enable a continuous in situ monitoring of analyst and physiological parameters. To minimize the physical trauma to the tissue during the probe insertion, the sensing portion 104 is terminated with an appropriately configured non-traumatizing tip 116 having a smooth curved surface, as further discussed below. The sensing portion 104 may carry distance markers 118, such as evenly-spaced graduated markers, on its outer surface 120 that are perceivable either by a human operator or with the use of machine-vision equipment during the course of the measurements, thus allowing for determination of the depth at which the sensing portion 104 has been inserted into the tissue.

The harnessing portion 112 may be configured to include a rugged and flexible tube 112b with a smooth outer surface that securely encloses both the optical and the optional electric instrumental extensions (no shown) of the at least one FO-based analyte sensor and the physical-parameter sensor of the sensing portion 104 and that is appropriately bonded inside the anchoring portion 108. In an embodiment that is devoid of the anchoring portion 108, the harnessing portion may be directly affixed to and accommodate the proximal end 104b of the sensing portion 104. It is contemplated that the sensing portion 104 may include various FO-element-based analyte sensors such as, for example, a pH sensor, a partial pressure of oxygen ($pO_2$) sensor or a partial pressure of carbon dioxide ($pCO_2$) sensor.

The anchoring portion or module 108 may include a commercially-available medical-grade Y-connector 108a. The tube 112b and the instrumental extensions of the portion 104 sensors pass through a straight portion 108b of the Y-connector 108a but are tightly and securely sealed at a joint 108c. The joint 108c includes a freely-rotating luer 108d configured to make a leak-free connection at the joint 108c and to allow for the rotation of the sensing portion 104 in either a clockwise or counter-clockwise direction with respect to the axis 104a. An angled-port of the anchoring portion 108 provides a standard perfusion port and a channel to facilitate a free-flow of fluids to and from the vicinity of the sensing probe 104 embedded into the biological tissue. In a related embodiment, the Y-connector 108a may be replaced with a different anchoring configuration. For example, in an embodiment of the probe adapted to be injected subcutaneously (not shown), where no fluids are required to be dispensed or sampled out around the embodiment, the anchoring configuration may employ a soft patch-like polymer or a clip, which may be useful to retain the probe on body parts (e.g. on a tongue or in an ear). In an alternative embodiment (not shown), a different anchoring option may be employed containing a patch with or without a utility channel traversing the patch throughout and connected to an auxiliary needle or catheter fitting.

In intra-arterial applications of the probe, which require insertion of the sensing portion of the probe in a blood vessel such as a radial artery around the wrist area (for monitoring, for example, blood gases of critically-ill patients), a lure with a working channel must be used. The introduction of the sensing portion of the probe into the artery is carried out by fishing the sensing portion through the catheter channel, which is pre-inserted into the blood vessel. The purpose of the catheter is to have the ability to sample blood intermittently, to provide a channel for administering of medication and other fluids, and to have a channel to monitor the artery's blood pressure. The lure 108d hooks up securely to the head of the catheter and provides a continuously operating working channel via the standard medical grade Y-connector 108a. In a different application, where a patient could be experiencing a shock, where blood flow in main blood containers contracts substantially and complicates to access for blood sampling, bodily analytes can be monitored subcutaneously through a needle or a catheter. On the other hand, in applications where no catheter or needle hook up is needed, such as, for example, insertion of the sensing portion of the probe in body cavities, a patch- or a clip-employing embodiment may prove to be more practical.

In further reference to FIG. 1A, a ruggedized FO-tether cable 122 may be employed to provide an operational communication between the embodiment 100 of the probe and a based unit when the base unit is remote. The tether 122 may contain an electrical conductor configured to electrically connect a physical-parameter sensor of the sensing portion 104 with the base unit. The end of the tether 122 proximal to the base unit is securely hard-wired therein, while its distal end is mated to the connector 112a thereby assuring a physical and optical contact between the sensing portion 104 and the base unit. In a related embodiment (not shown), however, the base unit may be positioned near the location of testing and connected directly to the probe 100 via the connector 112a. Alternatively, the base unit may be connected to the probe 100 through am optical module that is external to the base unit and is residing at the locations of the patient. Such external optical module can be connected to the base unit either via an electrical cord, or wirelessly via a telemetric channel, providing for a mobility in an emergency environment such as hospital, ambulatory, or tissue testing in a field environment.

FIG. 1B schematically shows a generalized embodiment 150 of an in-situ continuous monitoring system (ICMS) employing an embodiment of the sensing probe such as, for example, the embodiment 100 of FIG. 1A. FIG. 1C provides details of the generalized embodiment of FIG. 1B.

The tree schematics of FIGS. 1(B, C) show that the embodiment of the sensing probe is connected, through its proximal end and a communication channel, to a base unit 152 that has an optical module 154, 154' including at least one light source, an optical detecting module, and various optical elements and components that shape, filter, or gate illumination such as, for example, steering and beam-splitting optics, and optical filters. The optical module may be configured internally, 154, to the base unit 152 or, alternatively, as an external optical module 154' that is connected remotely (e.g., wirelessly) to the base unit 152. The remote connection of the optical module to the base unit is configured via a communication channel which either includes a direct connection through, e.g. and electrical cord with power and signal delivery strands or through a wireless telemetry with the transmitted subassembly integrated with the remote optical module and a receiver built into the base unit.

Additionally, the base unit 152 includes electronics, computer processor and tangible computer-readable storage medium with computer program product including appropriate program codes thereon that facilitate data processing. Peripheral devices and components of the base unit 152 include but are not limited to a display such as a monitor and/or a printer facilitating visual representation of the results of data processing to the user and a calibrator configured to calibrate the probe to make it compliant with industry standards. The sensing probe such as the embodiment 100 including the sensing and harnessing portions as discussed above, is connected to the base unit 152 via a tether cable 122 through the optical connector 112a, or to a remote optical module and, through it, to the base unit 152 and includes various FO-element based sensors 158 containing at least FO-elements that are appropriately housed and sealed within a housing structure of the sensing portion, as described further in this application.

Embodiments of the sensing probe of the invention may have at least one of biocompatible anti-thrombogenic (AT) characteristic, an anti-viral (AV) characteristic, and anti-inflammatory (AI) characteristic. Embodiments of the sensing probe are adapted to be inserted into a biological tissue of interest (such as a bodily vessel, organ, a tumor, wart, or acne, abscess, wound) and, once inserted, to continuously and in real-time monitor and measure various analytes and physical parameters associated with the tissue such as, for example, levels of oxygen, carbon dioxide, pH, sodium, potassium, glucose, lactate, temperature, pressure, either in vitro or in vivo.

Figure 2A:
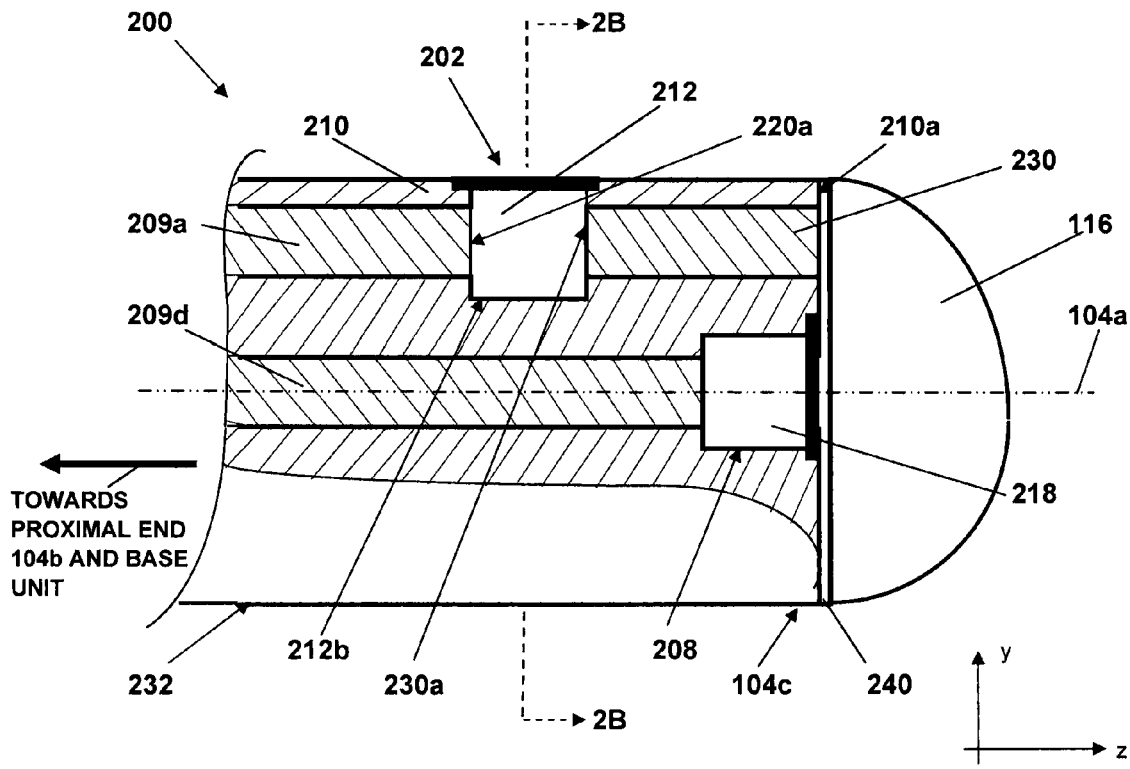
FIG. 2A: partial cross-section in side view.
Figure 2B:
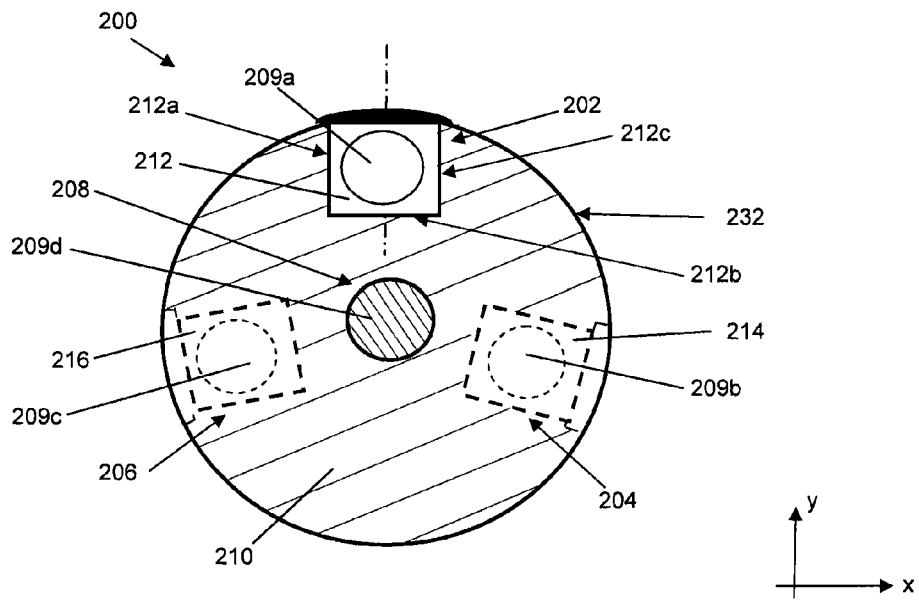
FIG. 2B: cross-section of side view of FIG. 2A.

FIGS. 2(A, B) show an exemplary embodiment 200 of the sensing portion 104 in cross-sectional side view and front view, respectively. As illustrated, the embodiment 200 contains four FO-based sensors: three peripherally-disposed sensors 202, 204, and 206 (configured to detect causes such as analytes, pressure, or temperature), and, optionally, an axially-positioned temperature sensor 208. The sensors 202, 204, 206, and 208 are disposed inside an embedding structure 210 having an elongated body preferably made of a polymeric material that encapsulates the sensors. Each of the sensors 202, 204, 206, and 208 includes at least one corresponding FO-element (elements 209a, 209b, 209c, and 209d) and a corresponding chamber (chamber 212, 214, 216, and 218) filled with an indicator-matrix appropriately chosen to facilitate monitoring of a predetermined analyte or a physical parameter. Embodiments of the optional axially-positioned temperature sensor 208 are described in detail elsewhere in this application. The body of the embodiment 200 is cylinder-like and has a circular cross-section, as shown in FIGS. 2(A, B). Generally, however, transverse cross-section of the elongated body of the embedding structure of a probe's sensing portion is not limited to any particular geometry. It may be elliptical-like, rectangular-like, triangular-like, or any other appropriate cross-section configured as may be dictated by a specific application. As shown in FIG. 2A, the embodiment 200 incorporates the tip-end 116 integrated with or affixed to a terminating surface 210a of the body of the embedding structure 210. While the tip terminating an embodiment of the sensing portion 104 of FIG. 1A does provide certain advantages in operation of the probe (for example, it reduces a trauma due to insertion of the probe into a biological tissue), the presence of the tip is not generally required. For example, in a related embodiment (not shown) the sensing portion 104 may be devoid of an non-traumatizing tip such as tip 116 and may be limited, at the distal end 104c, by the terminating surface such as the surface 210a. The terminating surface is generally curved, but in a simplest embodiment is a planar surface that is either perpendicular or inclined with respect to the axis 104a.

In further reference to FIGS. 2(A, B), the judicious configuration of the chambers within the elongated body, as discussed below, facilitates the optimization of performance of the embodiment 200 and offers advantages over related art. For simplicity of illustration, each of the FO-elements 209(a, b, c, d) respectively corresponding to the sensors 202, 204, 206, and 208 is shown in FIGS. 2(A, B) as a rod-like component, without differentiation between cladding and core portions of a corresponding fiber optic. Each of the FO-elements 209(a, b, c, d) is embedded or cast within the molded body of the structure 210 and is configured as an optical communication channel, within the embedding structure 210, that assures the optical connection between the base unit (not shown) of the embodiment 100 of FIG. 1A, the proximal end 104b, and the corresponding cavity filled with an indicator-matrix. Each of the cavities 212, 214, 216, and 218 has at least one wall defining the extent of the cavity within the embedding structure 210 and a position of such cavity in relation to a corresponding FO-element. For example, the chamber 212 associated with the sensor 202 is at least partly defined by walls 212(a-c). As shown, the sensor 202 includes a first FO-element 209a with an end-facet 220a cast within the structure 210 between the proximal end 104b and the chamber 212. The FO-element 209a terminates at a wall of the cavity 212 such that the end-facet 220a being positioned at a wall defining the cavity 212.

An embodiment of a given sensor of the invention may include an additional FO-element. For example, the sensor 202 is shown to contain an FO-element 230 disposed between the cavity 212 and the distal end 104c of the embodiment 200 such that an end-facet 230a of the FO-element 230 is aligned with a wall of the cavity 212 thereby terminating the FO-element 230 at the wall of the cavity 212. Any other FO-element-based sensor of an embodiment (such as the sensor 204 or the sensor 206 of the embodiment 200) may be configured in a similar fashion. Alternatively, in a specific embodiment an FO-element-based sensor may contain only a single FO-element terminating at a wall of the respectively-corresponding cavity It is appreciated that a FO-element-based sensor of the probe of the present invention generally includes a single straight FO-element or a succession of coaxially and co-linearly disposed straight FO-elements (such arrangement, for simplicity is hereinafter referred to as a series of FO-elements) and at least one chamber that corresponds to such FO-element(s) and that contains a judiciously chosen analyte-specific or physical-parameter indicator-matrix. For the purposes of the following description, a particular chamber can be denoted as an in-line chamber or an end-line chamber. These descriptors represent a position of the chamber with respect to corresponding FO-element(s). Simply put, if a chamber is located between two FO-elements in a series, the chamber is referred to as an in-line chamber. On the other hand, when a chamber optically communicates with and corresponds to a single FO-element, it is located at an end of such element and may be denoted as an end-line chamber. It is also noted that either an in-line chamber or an end-line chamber may define an aperture in a side-surface of the embedding body of the sensing portion, and such an aperture may contain an analyte-permeable membrane. Chambers defining apertures in the side-surface of the sensing portion correspond to sensors that are located in a peripheral portion of the sensing probe. An axially-located sensor such as a temperature sensor, on the other hand, has an end-line chamber associated with it, which is disposed in a distal end of the sensing portion of the probe (near the non-traumatizing tip) and which has an opening sealed with a non-permeable membrane (or a patch). In reference to FIGS. 2(A, B), the chamber 212 is an example of an in-line chamber (of the peripherally-located FO-sensor 202) that defines an aperture in a side surface 232 of the embedding structure 210. The chamber 218 of FIG. 2A provides an example of an end-line chamber of the axially cast temperature FO-element-based sensor 208.

In reference to FIGS. 3(A-D), a chamber 302 is an in-line chamber having an opening towards the side surface of the embedding body 320 of an embodiment 304 that contains a single peripherally-located sensor. This single sensor includes a series of FO-elements 306A, 306B each of which is spatially-coordinated to have its corresponding end-facet at a wall of the chamber 302. A chamber 312, on the other hand, is an end-line chamber having an opening towards the side surface of the embedding body 330 of an embodiment 314, which contains a single peripherally-located sensor. The single sensor of the embodiment 314 includes a single FO-element 316 spatially coordinated with the chamber 312 to have an end-facet of the element 316 at a wall of the chamber 312. The body 330 is shown to be wrapped in a tubing sheath 332, while the embedding body 320 of the embodiment 304 is optionally devoid of a tubing sheath.

It is appreciated that the idea of the invention does not, generally, impose a limitation on the number of optical communication channels and/or sensors incorporated within a particular embodiment of the sensing portion of the probe.

In a preferred embodiment, FO-element(s) of the invention is configured as either all-polymeric, or glass-on-glass, or polymer-on-glass fiber strands (the latter two also referred herein as glass-based FO-elements) disposed in a predetermined symmetrical orientation with respect to the longitudinal axis, of the sensing portion, such as the axis 104a of the embodiments of FIGS. 1, 2A. Generally, however, the symmetrical positioning of the fibers with respect to the axis of the sensing portion of the probe is not required. Each of the fiber strands is commercially available or custom-made and characterized by various opto-mechanical parameters describing at least the core, the cladding, and the numerical aperture of the FO-strand as known in the art. Each of the FO-elements is configured to operate, on one hand, as an independent light-delivery channel optically-connecting an optical module of the base unit and an indicator-matrix disposed within a respective chamber and, on the other hand, as a reference defining the location of the respective chamber. In manufacture, as discussed elsewhere in this application, the outer surface of a given FO-strand is cleaned, primed, and optionally coated with an appropriate color-coded (in a specific embodiment, an optically-opaque) coating prior to the embedding of the strand in an embodiment of the probe. These processing steps facilitate stronger bonding between the material of the embedding structure and the FO-elements and improve visibility and identification of the FO-strands during the formation of the chambers, thereby increasing the fabrication yield. Additionally, such processing facilitates the reduction of interference of light propagating in different FO-strands among each other and the surrounding environment. In a specific embodiment, FO-elements that cooperate with end-line chambers may be initially disposed inside thin-walled polymeric optionally color-coded tubes or sleeves and then, together with the sleeves, embedded into a body of the sensing portion, at least a proximal end of which may be enclosed within another thin-walled tube.

Figure 4A:
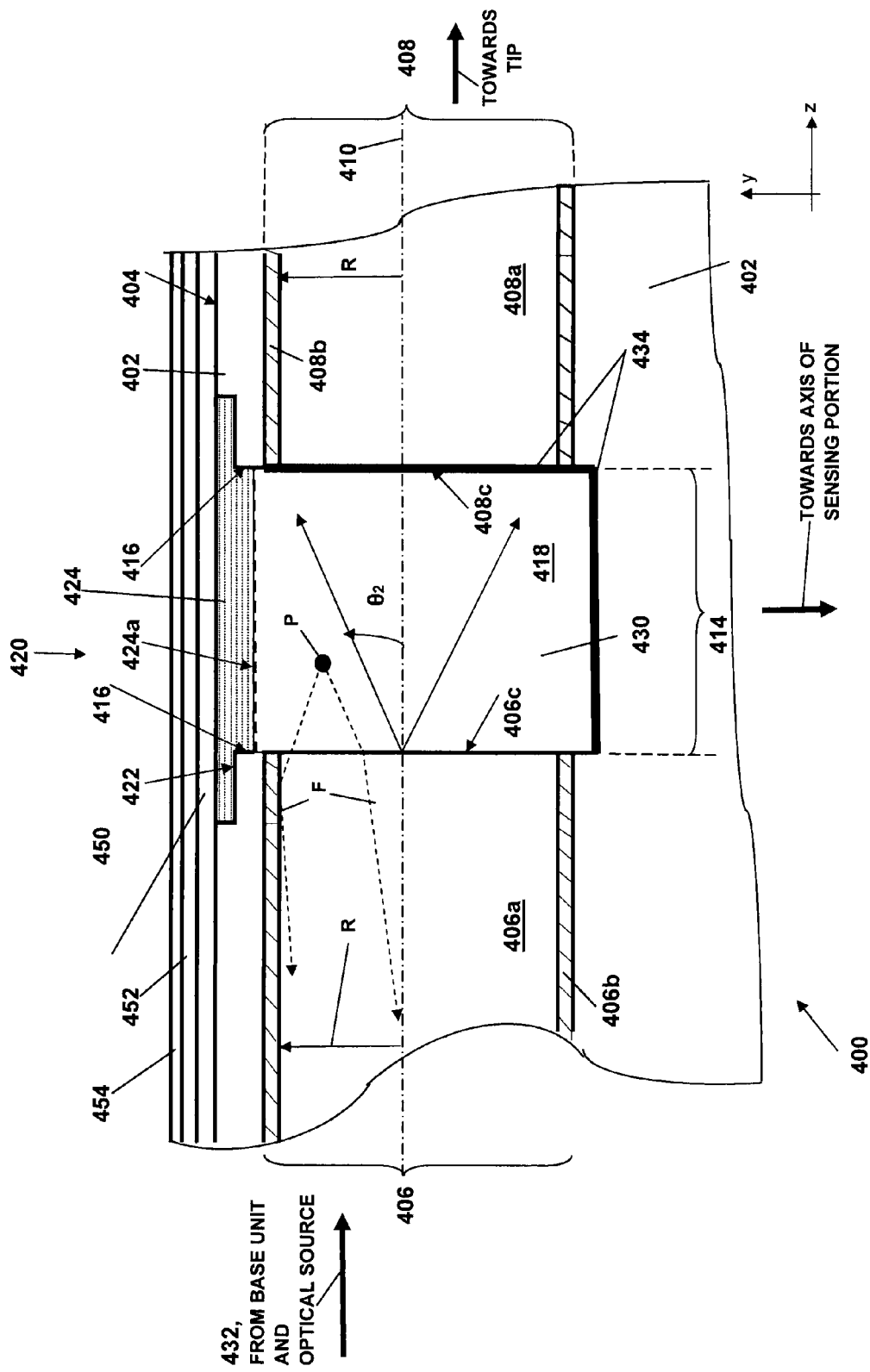
FIG. 4A illustrates a fragment of the sensing portion of the probe with a peripheral sensor including an in-line chamber that defines an aperture in a side surface of the embedding body of the probe, a permeable membrane enclosing the indicator-matrix inside the chamber, and auxiliary optical and physiological coatings.
Figure 4B:
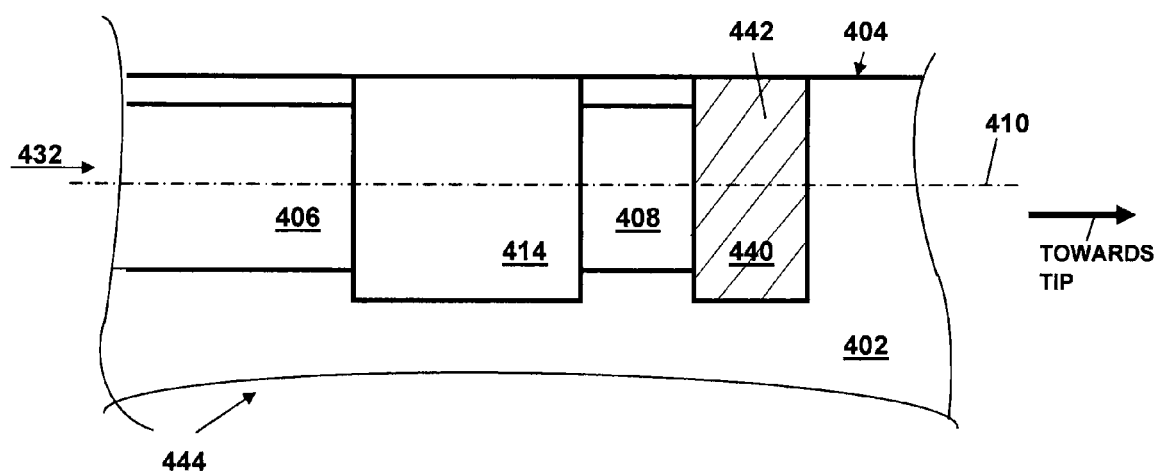
FIG. 4B shows a fragment of another embodiment of the peripheral sensor having an in-line chamber and an auxiliary chamber configured to enhance the optical performance and sensitivity of the sensor.
Figure 5:
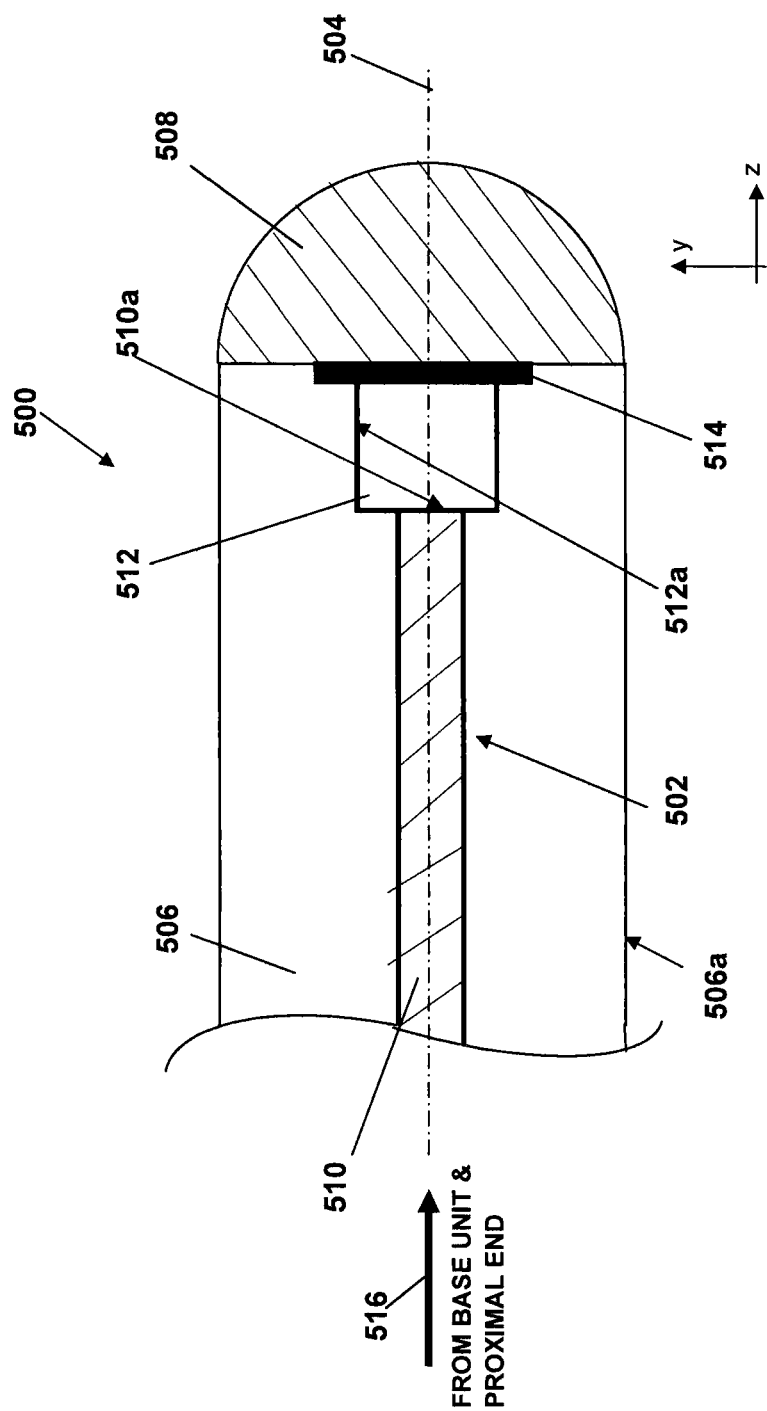
FIG. 5 shows an embodiment of a temperature sensor configured in the axial region of the embedding body of the probe and having an end-line chamber.
Figure 6A:
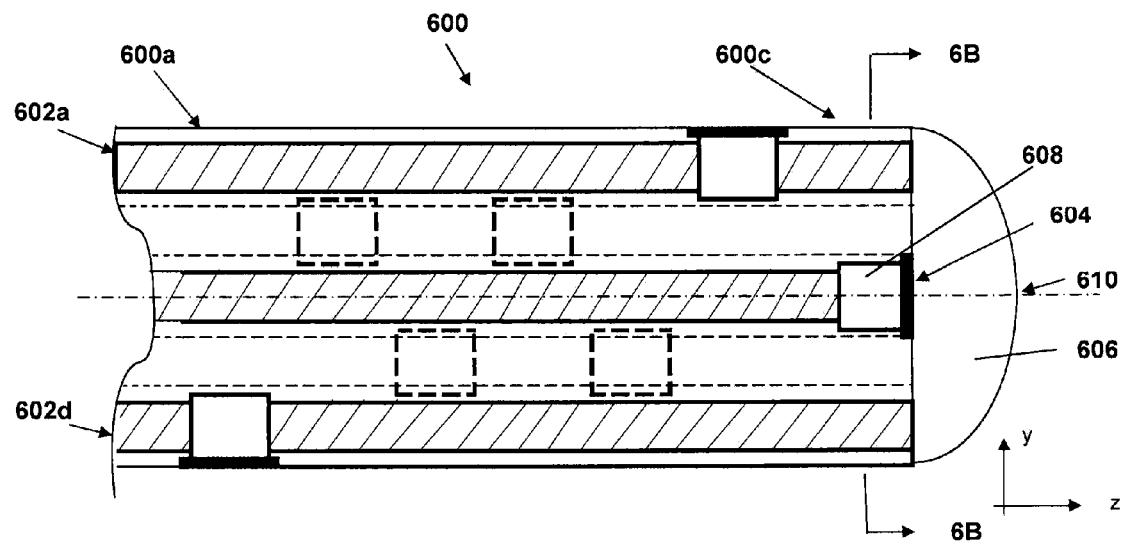
FIGS. 6(A, B) illustrate an embodiment of a multi-sensor sensing portion of the probe, in side and front cross-sectional views, respectively.

Further structural and operational details of embodiments of various chambers of the sensing portion of the probe are discussed in reference to FIGS. 4 through 6. In general, at least one chamber of an embodiment is configured to provide a cavity, in the embedding body of the sensing portion that defines a wall through which such chamber cooperates both optically and mechanically with at least one corresponding FO-element of the sensing portion. In addition, this chamber defines an aperture at the side surface of the embedding body through which access can be gained from the ambient medium outside of the sensing portion of the embodiment to the inside of the cavity. The aperture also facilitates chemical and physical communication between an indicator-matrix disposed within the cavity, in optical cooperation with an end-facet of a corresponding FO-element, and ambient medium. A communication between the indicator-matrix and the analyte is configured through an analyte-selective membrane placed in an aperture in the side surface of the embedding body as defined by the opening of the chamber. In addition, some embodiments may include a chamber corresponding to a temperature sensor located centrally within the sensing portion of the probe, as described below.

FIG. 4A, for example, illustrates a cross-section of a peripheral fragment 400 of an embodiment of the sensing portion of the probe that includes a body 402, having a circular cross-section and an outer surface 404, and contains first and second FO-elements 406, 408 disposed co-axially with respect to a local axis 410 of symmetry of the FO-elements. Each of the elements 406, 408 is an optical fiber with a corresponding core 406a, 408a having a refractive index $N_1$ and a radius R and a corresponding cladding 406b, 408b having a refractive index $N_2$. The body 402 is adapted to include an in-line chamber 414 having a wall 416 defining a cavity 418 and an opening 420 connecting the cavity 418 with a medium outside the outer surface 404. The FO-elements 406, 408 and the chamber 414 are configured such that end-facets 406c, 408c of the FO-elements 406, 408 terminate the FO-elements at the wall 416.

Generally, in an embodiment employing several FO-element-based sensors and respectively corresponding several chambers, a given chamber's location may be described with a set of coordinates with respect to, for example, an origin point corresponding to the apex of the non-traumatizing tip. The set of coordinates includes an axial coordinate (z) along the axis of the sensing portion of the probe, an angular coordinate (Θ), and a radial coordinate (r) with respect to the axis of the sensing portion. While the geometry of a chamber may vary from one sensor to another, in one embodiment the chamber may be shaped as a cuboid. In another embodiment, the chamber may be shaped as a trapezoid having larger dimensions at a side corresponding to the outer surface of the probe. In a related embodiment (not shown), the cavity of the chamber may be cylindrical. In yet another embodiment, the chamber may have any other volumetric shape as long as a wall of the chamber at which a FO-element terminates is tangentially perpendicular to the optical axis of the FO-element. In a specific embodiment, an axis of such FO-element passes through the center of the chamber.

In further reference to FIG. 4A, the opening 420 preferably has a recess 422, configured inwards from the outer surface of the surface 404, in which is disposed a polymeric analyte-specific membrane patch 424 permeably separating the specific analyte in the ambient medium from the contents of the chamber 414. While the depth and length of this recess may vary depending on the dimensions of the chamber and the type of the membrane patch used, the recess should be shallow enough not to reach the cladding of the corresponding FO-element. In operation, the cavity of the chamber is at least partially filled with an indicator-matrix material. The dashed line 424a defines the extent of the membrane patch 424, which, at the same time, seals the indicator material within the cavity 418 so as to prevent the indicator from leaking out of the chamber 414 and to satisfy the requirements of invasive medical applications. In one embodiment, the recess 422 configured during the fabrication of the chamber 414 as described below proves to be an advantageous element facilitating an increase in mechanical stability of positioning of the membrane patch 424 in the opening 420. The recess 422 allows to optimize the adhesion of the membrane patch to the chamber 414 and to reduce any bulk (bulge) build-up of the patch membrane material above the chamber 414.

In addition to the filtering membrane patch 424, an embodiment of the invention may include at least one additional analyte-specific membrane coating. For example, in an embodiment configured to monitor parameters of a gaseous substance (e.g., $pO_2$), the patch 424 may be characterized by hydrophobic properties. Such hydrophobic membrane, then, may be additionally coated with a hydrophilic layer of analyte-selective membrane coating 450 deposited directly onto at least the outer surface of the patch 424 and the tip (not shown) of the sensing portion. The hydrophilic layer 450 is sufficiently thin to maintain a relatively fast sensor-response and spatially extends over the area, of the outer surface 404, that covers the membrane patch 424 and, optionally, the extent of the FO-based sensor, thereby additionally smoothing the joints between surfaces of the patch 424 installed in the aperture of the outer surface 404 and the outer surface 404.

The hydrophilic layer 450 may be optionally overcoated with an opaque coating 452 (which may also be hydrophilic) and a protective coating 454. These coatings are designed to allow the free passage of the physical or chemical parameters to be sensed. The opaque coating 452 acts as an optical shield that blocks ambient and scattered light from interfering with the optical signals collected by an optical channel of a given sensor. In a preferred configuration, the coating 452 is made of opaque materials such as powders of $TiO_2$, graphite, or carbon black.

The protective biocompatible coating 454, on one hand, may possess AT, AV, and/or AI characteristics and thus promote a prevention of a build up of composites generated by the ambient medium, in which the probe is dwelling, during the operation. Examples of materials for making anti-thrombogenic reagents or coatings such as the coating 454 include but are not limited to synthetic polymers, heparine and its salt complexes, heparine compounds, derivatized cellulose with long chain alkyl chains and/or hydrogels. The layers of these anti-thrombogenic reagents are cast from mainly polar solvents such as alcohols, except in those cases where a combination of solvents is applicable to dissolve the reagent. In some cases selective coatings material such as sol-gel matrices of different porousity, polymer gels and polymer membranes will have exterior coatings of heparine, dextran sulphate, nafion, polyethylene glycol or polystyrene suphones. These materials have been tested and examined earlier for their biocompatibility properties with soft tissues.

On the other hand, the coatings 450 and 452 boost durability and mechanical strength to inhibit or prevent the peeling of the membrane patch 424 off of the chamber 414 during the insertion of the embodiment 400 into the biological tissue and monitoring of the tissue's biophysical parameters. In one implementation, the coatings 452, 454 can be distributed to almost completely cover the outer surface of the sensing portion of the probe, or, alternatively, to cover an aperture in the side surface 404 through which the ambient medium and the contents of the chamber 414 are in fluid communication. It is preferred that a polymeric material chosen as supporting material for the indicator-matrix have high permeability to the target analyte of interest so that the sensitivity of the optical indicator material to the target analyte of interest is adequate for a chosen sensing application. The permeable materials may include cellulose acetate, cellulose acetate esters, hydroxy propyl cellulose (HPC), hydroxy ethyl cellulose (HEC) hydroxy ethyl methyl cellulose (HEMC), Kollidones or Providones, Hydrogels, siloxanes, dimrthylsiloxane polymer, a diphenylsiloxane polymer or derivatives of dimethylsiloxane copolymers, polysiloxanes, polycarbonate copolymers, polyurethanes(tecoflex), polyimides, polyacetates, polymethacrylates, polyvinyls, polyvinyl acetate, polyvinyl butyral, polyvinyl chloride acetate, ethyl vinylenedine copolymers, silicon, natural rubber, isoprene rubber, and PVC. Porosity, gas permeability, and flexibility, as well as, biocompatibility of such materials can be affected or regulated during their preparations. The thickness of a polymer patch, a polymer film, or a polymer membrane used to encapsulate or enclose the analyte-sensitive indicator-matrix including dye material inside the cavity that has to be appropriately chosen and controlled in order to produce quantitative and reliable sensing performance. The thickness parameters or porosity values of coatings or membranes preferably have unchanged values across the span of the coating over the in-line chamber and the extent of a particular sensor. The porosity, gas permeability, and flexibility of such membranes or coatings can be adjusted during fabrication by the addition of several components like water, methanol, ionic salts or mixed solvents.

Further to FIG. 4A, the chamber 414 is preferably oriented to have a cross-section, in a plane perpendicular to the axis 410 that is symmetric with respect to the axis 410. Volumetric and geometrical parameters of an in-line chamber are appropriately chosen to optimize the performance of the embodiment of the invention. Specifically, the in-line chamber 414 is configured such as to optimize the overlap between the cone of light 430, that emanates into the cavity 418 at an angle $\Theta_2$ from the end-facet 406c of the FO-element 406 extending between the optical source (not shown) and the wall 416 and that corresponds to at least one guided mode of the FO-element 406, and the volume of the cavity 418 filled with an indicator (not shown). As understood by a skilled artisan, the cone of light 430 is defined by the numerical aperture of the FO-element 406. In one embodiment, the geometry of the cavity 418 is defined so as to maximize this overlap.

The volume of the cavity 418 of the in-line chamber 414 has to satisfy the following requirements. It has to be small enough to fit within the limits of a geometrical design of the sensing portion of the probe and large enough to accommodate a substantial amount of an indicator material required to generate, in response to the interaction between the indicator material and the ambient medium, a fluorescence signal sufficiently strong for the reliable detection and characterization of the analyte or a physical parameter of the ambient medium. Additional considerations in determining the volumetric parameters of the in-line chamber include efficiency of loading the indicator-matrix material inside the cavity 418, maintaining the structural strength of the sensing portion of the probe above a certain threshold, functional and geometrical isolation among the adjacent in-line chambers, and optimization of the sensor's response time.

Another advantage over the related-art sensors provided by embodiments of the present invention is that controlling the dimensions of the in-line chamber of the invention assures a smaller variance in levels of fluorescent light delivered from the indicator of the in-line chamber to the optical detection unit, as statistically determined across a large number of probes. The proposed herein implementations of a chamber provide structural support to the loaded indicator-matrix and membranes and prevent them from wearing out or disengaging from the chamber during exploitation.

The optimization of the overlap between the cone of light 430 and the volume of the cavity 418 dictates that the axis 410 of the input FO-element 406 should preferably pass through the center of the cavity 418 and that the element 406 and the cavity 418 be preferably coaxial. that the transverse extent of the chamber 414 exceeds the dimensions of the diameter of the core diameter of the FO-element 406. Otherwise, a portion of the indicator material disposed within the cavity 418 outside of the cone of light 430, such as a portion containing a dye molecule P, may not be necessarily directly exposed to excitation light and, consequently, a lower fluorescence signal F will be captured by the FO-element 406. The degree of a return-signal (fluorescence signal) F optimization depends on the severity of misalignment between the abovementioned axes and the degree of asymmetry of the geometry of the in-line chamber 414.

By way of a non-limiting example and in reference to FIG. 4A, for a multi-mode PMMA optical fiber 406 having a core radius R of about 50 μm having a numerical aperture (NA) of about 0.5, and the indicator-containing medium with $N_3 \approx 1.5$ filling the cavity 418, the angle $\Theta_2$ defining the cone of light 430 is about $20^0$. The extent of the cavity 418 along the axis 410 is, therefore, its length $L = R/\tan \Theta_2 \approx 140$ μm. The intensity of fluorescent light F generated by the indicator within the cavity 418 and captured by the FO-element 406 can be estimated as $I = K \cdot C \cdot NA \cdot R^2 L$, where K is a constant and C is a dye-concentration in the indicator material, based on an approximate derivation from a formula for spontaneous emission (fluorescence) of A. Yariv, *Optical Electronics* (3rd edition, Appendix D, pg. 543, 1985).

In continuing reference to FIG. 4A, the indicator material disposed inside the cavity 418 of the chamber 414 can be generally selected to support difference photonic responses to the interaction between the indicator and the analyte of the ambient medium. For example, the optical performance of the indicator may include such effects as absorption, fluorescence, back scattering, reflection, refraction, polarization effects, change of phase of light, or change of index of refraction. Sensors of the related art have been recognized to suffer either from (i) sensor-generated light-signals that, when delivered to an optical detector, are insufficient for reliable detection and/or from (ii) sensor-generated light-signals that have unacceptably large variance of intensity (under otherwise equal light excitation and exposure to ambient medium). Embodiments of the present invention address and overcome this shortcoming. By way of example, in case when the indicator material is disposed within the cavity 418 to fluoresce upon being illuminated with the excitation light 432, the intensity of such fluorescence that is captured and channeled to the optical detection unit by the FO-element 406 can be optimized by appropriately coating at least a portion of an inner surface of the wall 416 of the chamber 414 with a thin-film layer 434.

In one embodiment, the layer 434 includes a thin-film coating that is reflective at least at wavelengths of the excitation light 432 and the excitation light that has been scattered within the chamber and, optionally, at wavelengths corresponding to the fluorescent light F. Such layer 434, therefore, facilitates re-circulation of the excitation light 432 within the cavity 418 thereby configuring the chamber 414 to provide a double-pass or even a multiple-pass for the excitation light 432, and boosting the generation of the fluorescent light F per unit of the excitation light intensity transmitted from the base unit. In addition, the layer 434 increases efficiency of collection of the fluorescent light F within chamber 414 by the capturing FO-element 406. In operation of the embodiment, the re-circulation of light allows the user to operate an optical source of the base unit at lower power levels. The boost in levels of fluorescence, resulting from multiple pass of the excitation light through the chamber, increases the signal-to-noise ratio (SNR) of the detection of the fluorescent light and reduces the cross-talk among adjacent chambers of the embodiment. In a related implementation, the layer 434 may include an opaque coating configured to reduce the optical cross-talk between the adjacent FO-elements and chambers disposed, within the body 402, in a parallel relationship to one another. Whether absorptive or reflective (which depends on the embodiment), a coating such as the layer 434 assures that levels of signals at which similarly-operating sensors of different probes perform are consistent with one another. The operation-enhancing coatings such as the layer 434 can be applied using high-precision liquid-dispensing or vapor-deposition equipment.

In a related embodiment, a similar optically-enhancing effect can be achieved by configuring an auxiliary in-line chamber such as a chamber 440 of an embodiment 444 of FIG. 4B. The auxiliary in-line chamber 440 is filled with a highly reflective compound 442 such as titanium dioxide, barium sulphate, or another reflective composition mixed with an appropriate host material and sealed, to reflect most of the excitation light 432 and the fluorescent light F that has passed through the primary chamber 414 and the FO-element 408. Alternatively, the auxiliary in-line chamber 440 may be filled with an opaque material absorbing light energy that does not find its way back to the FO-element 406.

In yet another embodiment, and in reference to FIG. 2A, a reflective and/or opaque layer 240 may be disposed at the terminating surface 242 of the sensing portion of the probe in lieu of an auxiliary chamber. In such a case the terminating surface 242 is polished to a fine grade, appropriately covered with the layer 240 and then sealed with an embedding compound having high thermal conductivity to form a non-traumatizing tip such as tip 116. Alternatively, a miniaturized flat reflective and/or opaque optical element may be securely bonded against the finely polished terminating surface 242.

FIG. 5 schematically illustrates a cross-section of a fragment of a sensing portion 500 of the probe containing a temperature sensor 502 disposed axially and centrally, with respect to an axis 504 of and within a body 506 of the axially-symmetric embedding structure terminated with a non-traumatizing tip 508 that, in the present embodiment, has an elliptical longitudinal cross-section. An outer surface of the body 506 is denoted as 506a. The thermal sensor 502 includes a FO-element 510 axially extending without bends from a proximal end of the sensing portion 500 towards an end-line chamber 512 that is defined by a wall 512a and preferably has a recess in a plane that is transverse to the axis 504. The relationship between the dimensions and positioning of an end-line chamber and a corresponding FO-element is generally subject to the requirements discussed above in reference to FIG. 4A. The cavity of the chamber 512 is filled with a temperature-sensitive indicator material (not shown) and sealed with a patch and then cast with a thermally-conductive potting material 514. To complete the configuration of the sensor 502 as a stand-alone optical thermometer, the calibration of the sensor against an industry-recognized standard may be additionally required.

To enhance the thermal conductivity of the embedding structure around the temperature sensor 502, an alteration of thermal properties of the material of the embedding structure may be implemented in building up the tip 508. For example, the tip 508 may employ a polymeric compound having mechanical properties similar to those of the material of the body 506 but higher thermal conductivity thereby enhancing a response time of the thermal sensor. The embedding material preferably includes commercially available polymeric potting compounds with specifications that are compatible with a probe fabrication processes according to the embodiments of the present invention, handling requirements, sterilization procedures, stability, as well as biocompatibility in the environment of probe use.

Further in reference to FIG. 2A, in an alternative embodiment, a pressure sensor may be configured by filling the chamber 212 with a pressure-sensitive indicator and sealing the end-line chamber with a environmentally-stable and pliable (gel-like) compound containing uniform concentration of micro-bubbles (created either by trapped air bubbles or packed polymer micro beads), or polymeric micro-beads that change their size when loaded into a chamber. When the dimensions of the micro-bubbles are comparable to the wavelength of excitation light, such micro-bubbles serve as scattering centers for the incident excitation light incident onto the compound from the light source through the proximal end of the probe. Changes in pressure external to the body 210 would induce a change in the size of the micro-bubbles trapped inside the chamber 212, and alter the intensity level of the scattered light in proportion to the changes in the external pressure. The back-scattered light, the intensity of which is characteristic of the changes in external pressure, is captured at an end-facet 210a of the FO-element 210 within its NA and delivered, in reverse direction, by the element 209a to the optical detector (not shown) at the base unit, which appropriately processes the back-scattered optical signal to compensate for the temperature dependency of the collected data. To complete the configuration of the sensor as a stand-alone pressure sensor, the calibration of the sensor against an industry-recognized standard may be additionally required.

It is appreciated that generally, an embodiment of a probe of invention may include a plurality of sensors. By way of example, in a specific embodiment configured according to that of FIGS. 2(A, B), the sensing portion 104 of the probe may contain four FO-element-based sensors, for example three FO-based sensors such as sensors 202, 204, and 206 configured to interact with analytes or physical parameters and one axially-located temperature sensor, which can either be an FO-element-based such as sensor 208 or thermocouple-based sensor (not shown). Each of the FO-element-based sensors includes a single strand optical fiber with an outer diameter OD=125 um+/−5 μm, and an OD of the sensing portion 104 may be about 550 μm+/−50 μm. In another embodiment containing two sensors (one for interacting with a chemical analyte and one temperature sensor), the OD of the sensing portion may be 300 μm+/−50 μm. Another embodiment may contain only a single-stand optical fiber forming a base for a sensor configured to operate in two modes, for example, to interact with a chemical analyte and to perform a role of a temperature sensor. In this case, the OD of the sensing portion may be about 200 μm+/−25 μm. Yet in another embodiment, where the sensing portion of the probe includes seven sensors (six sensors configured to monitor chemical analytes, optionally pressure, and temperature), the OD of the sensing portion would be 550 μm+/−50 μm. It shall be appreciated that FO-based sensors, of the related art, having the same OD of approximately 550 μm could contain no more that four sensors (three sensors for interacting with chemical analytes and one thermocouple).

Figure 6B:
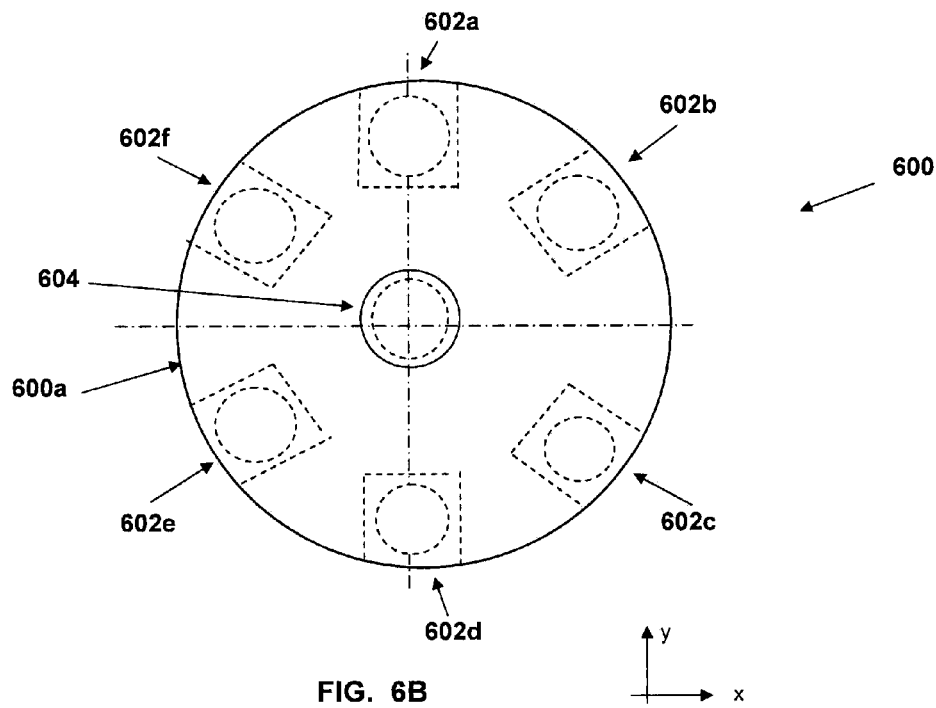

An alternative embodiment 600 of FIGS. 6(A, B) is shown to contain six peripheral FO-element-based sensors 602(a-g), each sensor configured to detect and monitor the presence of a particular analyte in the ambient medium, temperature, or pressure, an axially-disposed FO-element-based temperature sensor 604, and a non-traumatizing tip 606. The analyte-sensing and physical parameter sensors 602(a-e) are equipped with corresponding chambers distributed along the length of the sensing portion 600 and configured to contain appropriate indicators and dimensioned as discussed in reference to FIG. 4A. In reference to a cross-sectional view of FIG. 6B, it will be understood that the angular separation, across the cross-section of the embodiment 600, among the individual sensors responsive to analytes or physical parameters depends on the number of sensors employed. The angular separation between these sensors is preferably even and, by way of example, is about 60 degrees in the embodiment 600.

In a multi-sensor embodiment, generally, each of the chambers is disposed in-line with a corresponding FO-element at an appropriate location along the sensing portion of the body and has an opening at a side surface 600a of the sensing portion 6008, except for the end-line chamber corresponding to a physical parameter sensor that is disposed at a distal end 600c of the sensing portion 600. Each of the chambers is fabricated by carving out a portion of the corresponding FO-element and some of the embedding material around it or just the embedding material adjoining the end-facet of the FO-element. The end-line chamber such as the chamber 608 is manufactured, as further discussed below, by carving the central portion of the distal end of the sensing portion 600 and removing a longitudinal portion of the corresponding FO-element and, optionally, part of the surrounding embedding material.

Generally, in an embodiment adapted to operate with multiple analytes, the position of a particular chamber with respect to the vertex 610 of the embodiment depends on the type of a sensor to which this particular chamber corresponds. Sensors with hydrophobic (gas permeable, for example $pO_2$, $pCO_2$) membranes are preferably be located closer to the distal end 600c of the embodiment in comparison to the sensors employing hydrophilic (water permeable, for example pH) membranes. The latter chambers are preferably located closer, along the sensing portion 600, to the proximal end of the portion 600. The reason for such criteria relates to steps taken during the manufacturing of the sensors and designed to enhance the durability of the analyte-selective membranes associated with each chamber by introducing auxiliary over-coatings, as discussed in reference to FIG. 4A. A practical approach to fabrication of such embodiment is to recoat the body of the sensing portion, after the patch membranes have been installed in corresponding recesses of the openings of its in-line chambers, in a series of steps to preserve the selectivity criteria. Preferably, a sequential dipping technique is used to accomplish the task. To comply with such strategy, in-line chamber with hydrophobic overcoatings should preferably be placed towards the distal end 600c of the embodiment of the sensing portion. In-line chambers with hydrophilic overcoating would be preferably placed towards the proximal end of the embodiment. The first step in overcoating process includes dipping the sensing portion into a special hydrophobic coating material, starting with the distal end 600c and for the length of the sensing portion 600 such that the patch membrane corresponding to the most distal gas sensor is coated. Once this first coating is cured, the sensing portion is dipped in another overcoating material with hydrophilic properties to cover the remaining im-line chambers and respective membrane patches located more proximally with respect to the based unit. As a result of the sequential overcoating, each in-line chamber is overcoated with a universal hydrophilic coating layer such as the layer 450 of FIG. 4A and exhibits durable and exhibit smoother outer surface.

A temperature sensor such as the sensor 604 of FIGS. 6(A, B) is selected to be associated with the axially-disposed FO-element and is not required to come in direct physical contact with the ambient medium. The material of the tip of the probe is similar to the one used in the embedding structure, except it has a faster thermal conductivity property to reduce the response time in temperature measurement.

It is appreciated that, for compatibility with minimally-invasive biomedical applications, the largest practically useful OD of an embodiment of the sensing portion of the probe is determined by the inner dimensions of administering devices such as catheters and needles. For example, in blood gas monitoring application, the nominal inner diameter (ID) of a standard radial artery catheter (such as Arrow 20 Gauge) is about 900 um, which allows a continuous, intermittent or bolus infusion at a minimum of 16 ml/min. An embodiment of the sensing portion of the probe should be dimensioned to fit easily within such ID so as not to jeopardize the probe's integrity and to allow some left-over space around the body of the sensing portion for clinical interventions (such as infusion of a liquid into the container). The related art describes a 3-sensor probe employing a polymeric bent fiber optic element containing two strands of optical fiber for each sensor with a theoretically projected OD of 650 um. In practice, however, the OD of such a conventional probe is approaching 800 um due to excessive and uncontrollable build up of the membrane and coating materials on the outer side of the probe. In contradistinction, embodiments of the present invention employ a singe-strand FO-element for each sensor. The projected OD for a probe having a number of sensors equal to that of the related art, therefore, is only about 450 um. In one embodiment, the sensing portion of the probe can accommodate seven sensors within the body having the same OD of about 450 um. In another example, the related art describes a probe with a single trianalyte glass-based optical fiber enclosed in a body with a 600 um OD. While such embodiment is curious from a design point of view, its implementation and use begs a question of whether this embodiment is operationally feasible, as, in designing this embodiment, the effect of some well-known light-guiding principles appear to be either ignored or minimized. Whether or not such single fiber strand design is advantageous in the claimed application, when it comes to packing density, the expansion of the number of sensors on a single fiber strand remains problematic. In contradistinction, embodiments of the present invention advantageously employ multiple FO-elements thus scaling the functionality of the probe subject to ID of the administering device.

Present embodiments allow to accommodate, in a sensing portion of the probe, up to $N=\pi(D/(rD_f)-1)$ peripheral FO-element-based sensors with chambers having apertures at a side surface of the embedding body of the sensing portion, where $N_S$ is the number of FO-element based sensors (rounded to the nearest lower integer), $D_P$ is the OD of the embedding body, $D_f$ is the OD of the FO-element (optical fiber), and it is assumed that all optical fibers have equal OD, and r is a ratio of the chamber's width to the OD of the optical fiber. By way of example, a probe with the sensing portion having OD of less than 450 µm and r=1.5 will accommodate 6 peripheral sensors (analyte and/or pressure sensors) based on optical fibers with OD of 125 µm. If the central, axially-located temperature sensor is counted in as well, such an embodiment embeds a total of seven FO-element-based sensors.

Indicator-based chemical sensors and, in particular, the sensors employing fluorescence have been addressed in related art. For most of the fluorescence-based sensors, the intensity level of the fluorescent signal generated in response to the interaction between the indicator and the analyte is inversely proportional to the concentration of the analyte to be measured. This response, known as quenching, is described with a so-called Stern-Volmer expression $I_0/I=\tau_0/\tau=1+K_{SV}(Q)$, where $K_{sv}=k\tau_0$ is Stern-Volmer coefficient, k is a temperature- and solvent-dependant quenching constant, Q is quenching concentration, $I_0$ is fluorescence intensity in the absence of the quencher, I is fluorescence intensity in the presence of the quencher, $\tau_0$ is lifetime of fluorescence in the absence of the quencher, and r is lifetime of fluorescence in the presence of the quencher.

Indicator matrices (including dyes) are sensitive and respond quickly, continuously and reversibly to changes in concentration dynamics of a specific target analyte or physical parameter being measured. Reversibility of operation of a given sensor implies that, when the sensor is removed from the medium a parameter of which is being monitored, the sensor comes to its original, equilibrium state with respect to measurement of fluorescent light. Such indicator-matrix compounds may be referred to as active, while those that do not response to changes in their optical properties by the external analyte are denoted as passive. Changes in the level of fluorescence can be detected either by monitoring the changes in the fluorescence signal intensity level or the changes in the induced time-decay of the fluorescent signal or changes in phase-shift of the fluorescent signal with respect to the excitation light. Fluorescent light generated by the indicator inside a chamber is collected, with the use of an at least one reflective component or layer, as described above, and delivered by an FO-element of the embodiment to an optical module of the base unit, where it is detected and analyzed.

Some of the chambers of an embodiment may contain a distinct sensing and non-sensing photo-chemical indicator material. The level of fluorescence of the non-sensing indicator material is used to reference out most of the optical intensity fluctuations created within the sensor system, such as optical fluctuations associated with operation of the light source and/or optical detector, losses on transmission and coupling etc. Additional passive fluorescence signals generated by the non-sensing indicator material are used in signal conditioning and in carrying out the field calibration procedure.

In one embodiment, the indicator includes dye material that is either entrapped by or covalently bonded to a supporting matrix, such as supporting sol-gel material that prevents leaching and/or reduces the effect of photo bleaching of the dye due to its inherent characteristic and stable molecular structure. Covalent bonding implies that the dye molecules are immobilized, within the supporting matrix, via reactive functional groups. The supporting matrix is configured to permit interaction between the dye material and the analyte or substance to be detected and'or monitored. Analyte-permeable support matrices include various compositions not limited to sol-gels, hydrogels, membranes, micro-encapsulating or micro-embedding organic or inorganic material and porous cement-like matrix. In one example, sol-gel derived nanoparticles containing the required selective dye molecules can be utilized and processed at room temperature. Compared to other support media such as polymer membranes, or simple polymer gels or hydrogels, supporting sol-gel material offers specific advantages such as higher chemical, photochemical and thermal stability, mechanical strength, optical transparency, compatibility with various dyes, and biocompatible behavior for medical applications.

The dyes used in embodiment of the invention may be chosen from a large group of organic or inorganic materials such as metal-ligand complexes of ruthenium(II), osmium (II), iridium(III), and rhodium(III) ions with organic ligands like 2,2'-bipyridine, 1,10-phenanthroline, 4,7-diphenyl-(1, 20-phenanthroline0,4,7-dimethyl-1,10-phenanthroline, 4,7-disulfonated-diphenyl-1,10-phenanthroline, 5-chloro-1,10-phenanthroline, 5-bromo-1,10-phenanthroline, various alpha-diamine and thiazole and substituted thiazoles, and several platinum and palladium complexes of porphyrines and substituted porphyrines (for an example, tetraphenyl porphyrines as disclosed in "Emerging Applications of Phosphorescent Metalloporphyrins" *Journal of Fluorescence, Vol. 15, No. 4*, July 2005 (© 2005, by Dmitri B. Papkovsky and Tomas C. O'Riordan). The dyes may additionally or alternatively include complexes of phthalocyanine and substituted derivatives, unsubstituted and substituted derivatives of hydroxypyrenesulphonic acid (HPTS), visible light-excitable SNARF and SNAFL pH indicators, several crown ethers or modified crown ethers, quinolinium-based Cl⁻ indicators such as 6-methoxy-N-(3-sulfopropyl)quinolinium (SPQ), several ionophores like valinomycine, crown ethers, Monensin, BME-44 (for $K^+$), ETH 4120 (for $Na^+$), ETH 1001 and ETH 129 (for $Ca^{2+}$), and, liphophilic Diamides, azo dyes, absorption dyes such as phenol red, and bromothymol blue or chlorophenol red. The dyes can also be selected from a vast group of fluorescent dyes disclosed in the *Molecular Probes Handbook* (11th edition, published by Invitrogen Corp., Carlsbad, Calif. 92008). Embodiments of the present invention also contemplate the use of a support matrix to position the analyte-specific dye molecules inside the chamber or cavity.

The solid support materials are also contemplated for use with embodiments of the invention to either covalently bind the dye or link the dye molecules by letting the dye be adsorbed in the support material. Some examples of solid support materials are provided by aminoaryl-controlled pore glass (CPG), lithospheres particles of uniform size or Kieselgel (chromatography grade), or chromosorb, polymer such as XAD-4, Dow Sorb or other polymer based on PMMA derivatives, silicon based polymers like dimethylsiloxanes, and other substituted siloxanes with or without cross-linking agents.

In one embodiment, the preparation of an indicator including the dye material is done with a slurry, paste, or cement-like dough made with a support polymer or gel that is preferably non-ionic to prevent a chemical or physical interaction with dye molecules and chemical or physical interference with interaction between the indicator and the analyte. Examples of such polymers are hydroxy ethyl cellulose (HEC), hydroxy methyl propyl cellulose (HMPC), Methacol, Ethacol, Kollidones, Dextran, polyvinyl pyrrolidine (PVP), polyethylene glycols silicon fluids or polymethylsiloxanes or derivatives.

In one embodiment, dye molecules can also be encapsulated or entrapped or immobilized in a transparent substance which is directly exposed to light, where the substance is a glass-like solid such as a rigid sol-gel of a pre-defined porosity. (Adjustment of porosity may be achieved with the use of ionic salts such as $Zn^{++}$ and $Mg^{++}$ salts, or with the use of mixed solvents like methanol and acetone, or methanol and methylene chloride.) More specifically, it may be a material judiciously synthesized to encapsulate or bind sensing dye molecules of the indicator. The new methods of fabrication of such materials will result in a production of improved sensitivity of sensors. In a representative embodiment, the new support materials are used to immobilize fluorescence analyte specific indicators in a hydrophobic or hydrophilic matrix. An example is provided by the immobilization of oxygen sensitive platinum compound of custom-synthesized porphyrine derivative indicator and disposing the indicator in a cavity of the in-line chamber. Analyte-specific indicators coming from various groups such as transition metal ions and their ligand complexes, pure organic fluorescent compounds, or mixed ligands metal complexes, the excitation and emission spectra of which overlap with optical spectra of commercially-available light-emitting diodes (LEDs) that can be used as an optical source producing the excitation light.

The following is a description related to several specific embodiments of the invention.

The related art offers several techniques for optical measurement of glucose concentrations. These techniques include (i) the use of optical oxygen probes to monitor glucose oxidase reactions in which oxygen is consumed; (ii) the measurement of pH-changes in an enzymatic reaction; and (iii) the measurement of hydrogen peroxide in a peroxydase reaction or measurement of $NAD^+$ concentration in a dehydrogenase based reaction. Embodiments of the present invention employ a glucose dehydrogenase-based optical detection principle for developing optical sensor for measuring glucose in human tissue or interstitial fluid. In this approach, the concentration of glucose is directly measured by monitoring the fluorescence of NADH. In the presence of glucose dehydrogenase, glucose is converted to D-gluconolactone, and $NAD^+$ is converted to NADH. $NAD^+$ is not fluorescent, but NADH is. When NADH is excited in UV (peak maximum at 386 nm) it emits at 460 nm. Thus, the rate of consumption of glucose is a direct indicator of the fluorescence of NADH. The fluorescence intensity of NADH can be monitored by measuring the NADH fluorescence over time. In the present invention, uniform size of nanoparticles of poros glass or polymer is used to immobilization of glucose dehydrogenase for sensor fabrication. Two methods of immobilization are well known in the literature—(1) covalent immobilization and (2) coimmobilization of NAD and glucose dehydrogenase. These immobilized nanoparticles will be used to fill the cavity in the optical fiber and a selective membrane will protect the indicator-matrix in place for sensing of glucose:

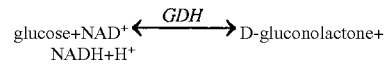

Embodiment of the present invention also contemplate method and system employing an optical lactate sensor capable of measuring and monitoring the lactate levels in patient blood, interstitial fluid or in tissue continuously and in real time, in intensive care units, without the need for a calibration procedure. Mainly, four enzymes are used for the detection and monitoring of lactate: dehydrogenase (LDH), lactate oxidase (LOD), lactate monooxidase (LMO), and cytochrome b2 (Cyt b2). The processes in three cases lead to pyruvate, and in the case of LMO, to acetate. Most of the electrochemical lactate sensors are based on the LOD catalyzed reaction for the detection of L-lactate:

The concentration of lactate can be directly measured by monitoring the fluorescence of NADH. In the presence of lactate dehydrogenase, the lactate is converted to pyruvate, and $NAD^+$ is converted to NADH. $NAD^+$ is not fluorescent, but NADH is. When NADH is excited with UV light (peak maximum at 386 nm), it re-emits light at about 460 nm. As a consequence, the rate of consumption of lactate may serve as a direct indicator of the fluorescence of NADH. The fluorescence intensity of NADH can be monitored by measuring the NADH fluorescence over time. In the present embodiments, uniform sizes of nano-particles of porous glass or polymer are used to immobilization of lactate dehydrogenase for sensor fabrication. Two methods of immobilization are known in related art: (1) covalent immobilization and (2) coimmobilization of NAD and lactate dehydrogenase. These immobilized nanoparticles may be used to fill the cavity in the optical fiber and a selective membrane will protect the indicator-matrix in place for sensing of lactate.

Figure 7A:
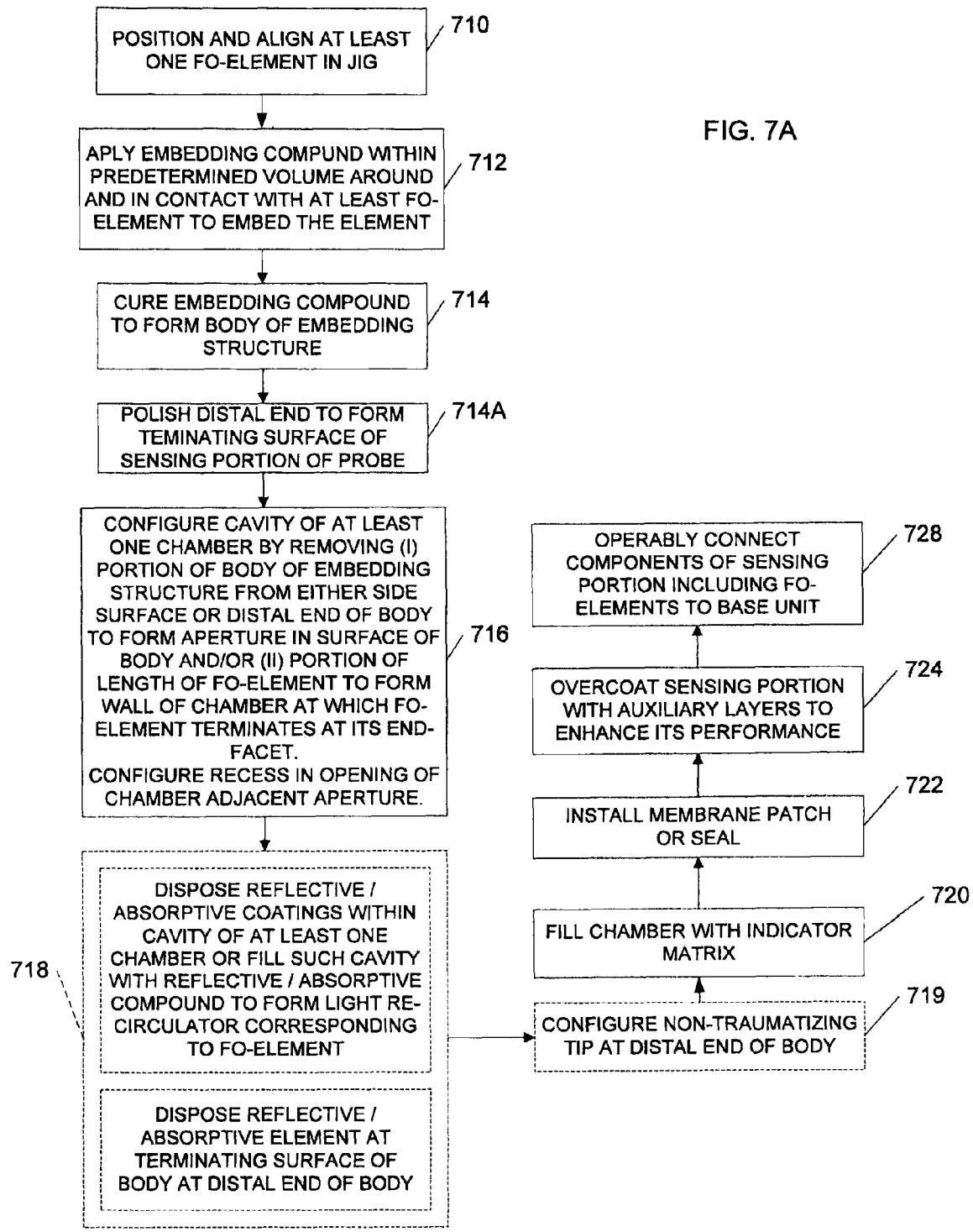
FIG. 7A is a flow-chart illustrating an embodiment of method of fabrication of the sensing probe of the invention.

According to one embodiment of FIG. 7A, a method of fabrication of an embodiment of the sensing portion of the probe (such as, for example, either of the embodiments of FIGS. 1A, 2, and 4-6) includes at least the following steps. At step 710, the appropriately chosen FO-elements are prepared and precisely positioned, aligned and secured with respect to one another in a predetermined linearly-parallel arrangement as a bunch, in a set-up jig. In case when several FO-elements are employed, the linearly-parallel arrangement implies that these straightened FO-elements are disposed parallel to each other with a predetermined spacing. The potting compound such as a UV-curing epoxy having appropriate specific viscosity and a curing characteristic is then applied, preferably gradually and uniformly, to the aligned bunch of the FO-elements, at step 712, within geometrical boundaries defining the cross-section of the embedding structure such as to cast the FO-element bunch within these boundaries. In one embodiment, the geometrical boundaries may be defined by a thin-walled tubing (made of, for example, a polymer) within which the aligned bunch of FO-elements has been secured at step 710. During the application of the potting compound at step 712, care is taken to leave loose ends of the FO-elements not covered by the compound at a proximal end of the bunch. Alternatively, when fabricating a probe with an end-line chamber, the prepared FO-elements may be individually potted inside separate, preferably color-coded thin-walled polymeric tubes having IDs that are slightly bigger than the ODs of the individual FO-elements. This method is preferred when glass-based FO-elements are used. For polyimide-coated FO-elements, the thin-walled tubes may not be required. Distal end-facet of each of the potted FO-elements is polished to a fine optical grade. The FO-elements are then aligned in a mutually parallel fashion to one another with their respective polished end-facets longitudinally displaced, at predetermined distances, with respect to one another.

At step 714, the epoxy is promptly cured with an optionally automated UV-wand so as to form a substantially straight and solid, with smooth and uniform cross-section and outer surface, elongated body embedding and supporting each FO-element. In a specific embodiment, the elongated body can be made flexible. While in a related embodiment a thermal curing epoxy and a thermal curing procedure can be chosen instead, as known in the art, the UV-curing process is particularly preferred when the employed FO-elements are made of polymeric materials because otherwise the application of elevated epoxy-curing temperature may affect and alter the mechanical integrity and optical characteristics of the FO-elements. When glass-based FO-elements are used, the embedding structure mechanically protects and cushions the FO-elements in the sensing portion of the probe against the damage that may occur during the handling of the probe. In a specific embodiment, the polymeric material used to configure the embedding structure 210 of FIGS. 2(A, B) may be translucent. For example, the polymer may be a commercially-available UV-curable biocompatible and sterilization-resistance brand of polymer such as Dymax, Electro-Lite Master Bond, and Loctite. The distal end of the formed embedding structure is then polished, at step 714A, to a fine optical grade along a predetermined surface (preferably along the plane perpendicular to the longitudinal axis of the embedding body).

The following processing steps are associated with configuring in-line and end-line chambers of the embodiment. In case of fabrication of an in-line chamber, a portion of the body of the embedding structure (including any thin-walled tube material) is removed, at a pre-defined radial position along the outer side surface of the embedding structure, in a digging-like procedure starting from the side surface inward with a chosen width and at such a depth as to take out not only a complete segment of a length of a FO-element (including both core and cladding portions) that is disposed underneath the surface but also a portion of the cured compound located deeper than the FO-element. The removal procedure may be accomplished as known in the art, for example with the use of laser ablation or etching. As a result, an in-line chamber is appropriately dimensioned as discussed in reference to FIG. 4A with a wall at which a portion of the FO-element terminates with an end-facet. In case of fabrication of an axial end-line chamber, a portion of the body is removed along an axis of the body starting from the distal end of the embedding structure inward, along its axis, and together with a longitudinal portion of the corresponding axially-located FO-element and the embedding material and any thin-walled tube material surrounding this FO-element such that a core axial portion of the embedding structure is taken out. As a result, the end-facet of the corresponding axially-positioned FO-element also coincides with a wall of the thus formed cavity. At this very step 716, an appropriate recess may be formed in the opening of the chamber leading to the outside of the embedding body through either a side surface of the body or through a distal end of the body by appropriately extending the opening.

At optional step 718, a chamber may be additionally configured by disposing a reflecting coating on its wall to provide for a light-recirculating element and/or absorbing coating to diminish back reflections such as, for example, an element 434 of FIG. 4A. In an alternative embodiment, where more than one in-line chamber is sequentially formed along to correspond to the same FO-element based sensor, the in-line chamber located closer to the distal end of the embedding structure may be appropriately filled with a reflecting and/or absorbing compound, as known in the art, to configure an alternative version of a light-recirculator such as that including elements 440 and 442 of FIG. 4B. At this same step, an optional reflector or absorber such as the element 240 of FIG. 2A can be formed at a terminating polished surface of the distal end of the embedding body. Optional formation of a non-traumatizing tip directly at the distal end of the body of the sensing portion may be accomplished at step 719.

At step 720, chambers are filled with an indicator-matrix in a predetermined sequence. In one embodiment, the indicator material is disposed within the chamber in physical contact with the end-facet of the FO-element terminating at the chamber's wall. In another embodiment, however, such contact may not be not required. At step 722, an appropriately shaped permeable membrane patch or a sealing membrane, depending on the type of the chamber, is installed such as to cover the opening and prevent the indicator material from leaking out of the chamber. Once the patch membranes/seals are cured, a hydrophobic coating may be applied, at step 724, to the surface of the segment the sensing portion that contains gas-monitoring sensors. The process of loading the indicator-matrix into a chamber, covering such chamber with a membrane, and overcoating the membrane may then be repeated for another chamber. Preferably, a chamber having a hydrophobic membrane is configured prior to a chamber having another type of membrane.

Another overcoat then may be applied with a hydrophilic layer that spatially extends from the distal end of the sensing probe towards the proximal end of the sensing portion such as to cover the fragment of the sensing portion containing all of the chambers. In addition, an opaque hydrophilic layer may be applied over the whole surface of the sensing portion of the probe. An embodiment of the method of fabrication of the sensing portion of the probe may include coating the outside surface of the sensing portion with various coatings that enhance at least one of fluid communication between the ambient medium and the indicator material inside a chamber, opto-mechanical characteristics, AT characteristics, AV characteristics, and AI characteristics of the probe, as discussed, for example, in reference to FIG. 4A.

The formed sensing portion of the probe is then placed in a judiciously chosen protective environment such as a cuvette containing a specifically designed buffer solution (SCF). Once the embodiment of the sensing portion of the probe has been formed, at step 728 the proximal end of the embodiment is appropriately anchored, shielded, harnessed and terminated with an FO-connector.

Figure 7B:
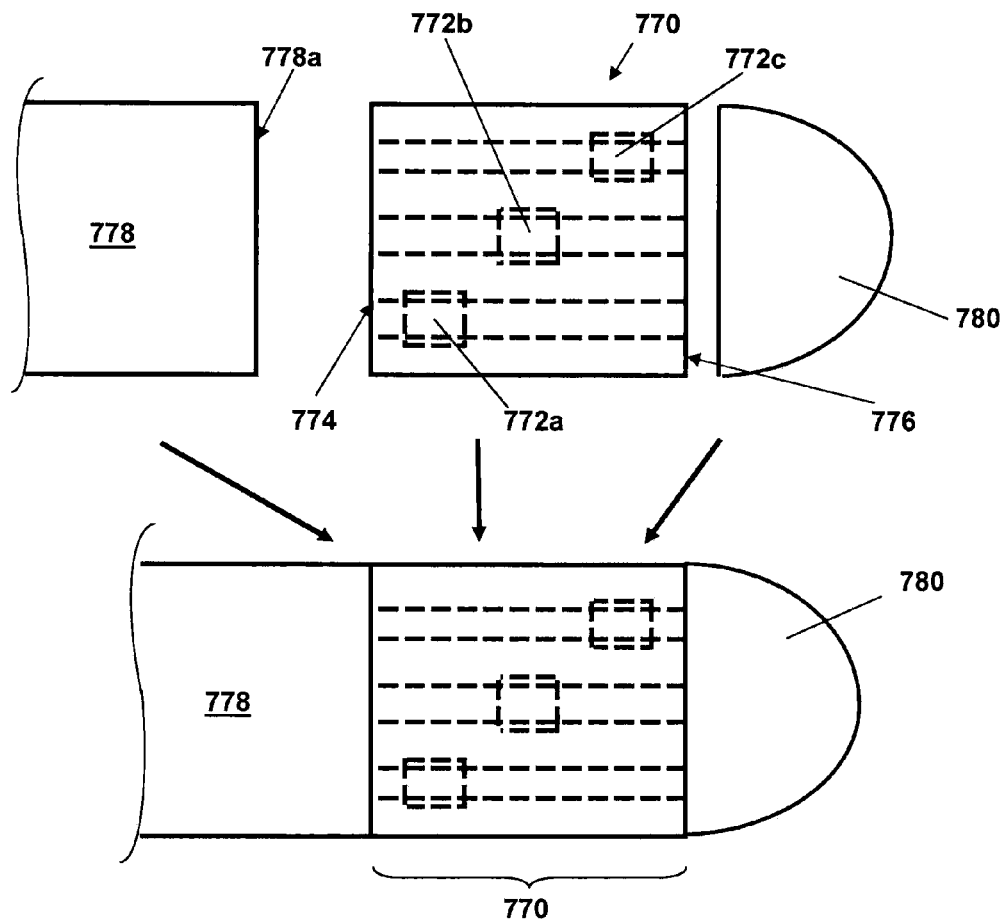
FIG. 7B illustrates an approach to mass-production of an embodiment of the invention.

In reference to FIG. 7B, a fragment of a sensing portion of the probe can be pre-manufactured in a separate processing cycle to incorporate the sensing chambers and can be later bonded to and assembled with remaining portions so as to form a complete probe, thereby facilitating mass-production of an embodiment of the probe. For example, a fragment 770 can be fabricated by forming a body of the sensing portion that embeds or casts the molded therein FO-sensors (including the FO-elements and corresponding chambers such as chambers 772(*a-c*)) according to a method described in reference to FIG. 7A. The end facets 774, 776 of the segment 770 are polished flat according to optical specifications. The prepared segment 770 can be later affixed to or integrated with another pre-fabricated fragment 778 of the sensing portion, located proximally to the anchoring portion (such as portion 108 of FIG. 1A) of the probe. The fragment 778 has a terminating surface 778*a* that is polished with optical quality and includes uninterrupted embedded or cast FO-elements, the number and disposition of which within the embedding body of the fragment 778 appropriately corresponds to those of the FO-sensors of the fragment 770. The integration of the fragments 770 and 778 may make use of precision marking and aligning techniques and index-matching adhesives and thin-coupling sleeves facilitating the alignment of individual FO-elements in particular and the embedding body of the sensing portion in general. Similarly, a tip 780 may be pre-fabricated independently, in a separate processing cycle, and later joined with the fragment 770. Embodiment of a sensing portion fabricated in the described fashion lends itself to being a stand-alone component capable of being directly inserted or attached to a remote optical module of the ICMS.

Precision and accuracy of operation of a sensing probe is recognized to be of critical importance. Just as any sensor, embodiments of the present invention, once fabricated, have to undergo a calibration process before they are packaged and sent out for sterilization. The lack of long-term operational stability of most of the sensors employing indicator matrices that operate in a changing fluid-based environment (e.g., within a blood container) forces the user to regularly recalibrate the sensors to accurately detect and monitor the concentration of an analyte or a readout of a physical parameter time and time again. To operate in a preferred linear regime, both bias and slope of the mathematical relationship relating each sensor's operational dependence on the variable parameter must be identified and registered. To determine a slope of the linear function, at least two independent data point are required. To this end, in order to obtain these data points, a typical factory calibration set-up includes a closed-loop gas-bubbling tonometry system in which a sensor has to be immersed in an environment where two steady-state stages of sensor parameter levels have been achieved. All registered data is document and logged to the traveler associated with that probe. The probe is packaged and sent out for sterilization and shelved for use prior to an expiration date. Prior to its use in a clinical environment, the probe has to be recalibrated for reason discussed earlier. Besides a burden imposed by maintaining a sterilized environment while running a calibration process in the field environment, calibration setups and procedures described in the related art are bulky, take long time and, therefore present a problem for attending clinicians. Indeed, in a critical-care environment patient status could escalate to critical sometimes within minutes. However, the two-point tonometry calibration schemes of the related art may require more than half-an-hour of calibration and a cumbersome calibration set-up that is hardly suitable for the critical-care clinical environment.

Embodiments of the present invention solve these problems by employing a combination of additional hardware such as a novel field-calibration jig, which may be configured to be reusable or disposable, and photonic-based calibration scheme. The jig contains cuvette-like small containers with judiciously chosen contents, as described below. Some contents serve the purpose of facilitating the two-point calibration procedure. In addition, embodiments of a two-point field calibration procedure employ a novel spectral extrapolation strategy compatible with the ICMS modules that the related art is not aware of.

Figure 10:
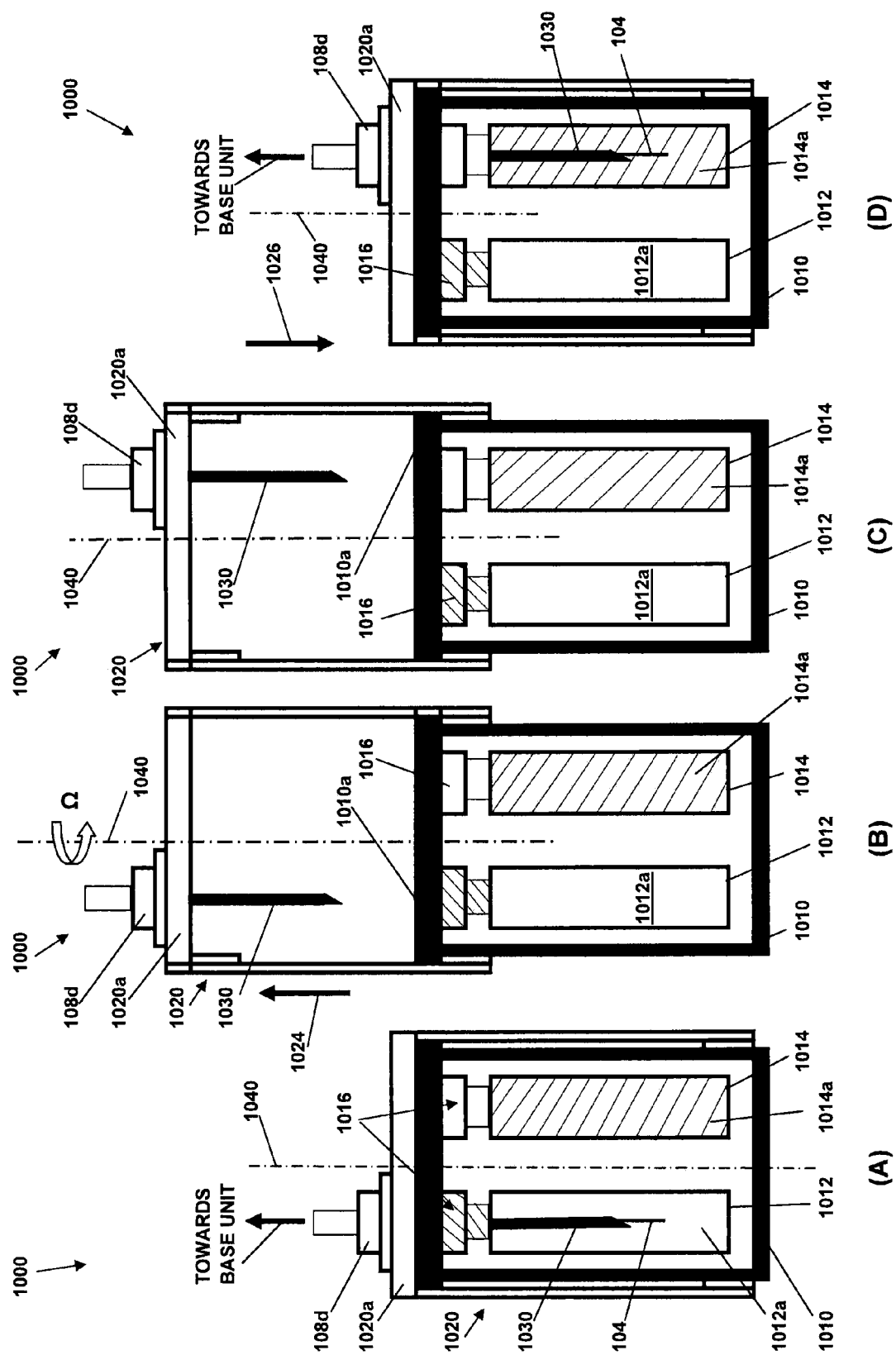
FIGS. 10(A-D) schematically illustrate embodiments of a field probe-calibration jig and a method of such calibration.

Embodiments of the invention include a controlled tonometered field calibration system utilizing a jig with moving (either manual or automated) parts to facilitate the secure removal and placement of the probe sensing portion from the travelling probe-dwelling container to a first buffer container and then to a second buffer container, thereby enabling at least two-point calibration check-up of the sensing portion 104 of FIG. 1A at constant temperature. In reference to FIGS. 10(A-D), showing, in side view, the steps of calibration of a sensing probe according to an embodiment of the invention, an embodiment 1000 of a calibration jig includes a hollow cylindrical body 1010 providing support for three cuvette-like containers (as seen in side views, containers 1012 and 1014. A third container, in which the probe travels, is not shown, for simplicity of illustration). These containers, in one embodiment, may utilize small drug bottles each sealed with a medical-grade fluid-impermeable rubber stopper 1016 with the use of standard medical sealing methods. The stopper 1016 is configured to receive the embodiment of the sensing portion of the embodiment with minimal friction. Each of the containers includes, under the seal 1016, a respectively corresponding buffer solution. For example, the container 1012 houses a stable and pre-tonometered buffer solution at a predefined calibration concentration 1012*a*, while the second container 1014 contains a different stable and accurately pre-tonometered buffer solution at a second predefined calibration concentration. The embodiment 1000 also includes a cylindrical jig-head 1020 dimensioned to fit on top of the body 1010 and configured to be smoothly repositionable along the length of the body 1010, as shown by arrows 1024, 1026, such that the embodiment 1000 is readjustable between two extreme positions. A first extreme position of the embodiment 1000 is illustrated in FIGS. 10A and 10D and is characterized by having a horizontal portion 1020*a* of the jig-head 1020 be in close correspondence with a top 1010*a* of the body 1010. A second extreme position of the embodiment 1000 is shown in FIGS. 10B and 10C, and is characterized by having the horizontal portion 1020*a* of the jig-head 1020 distanced from the top 1010*a* of the body 1010. In order to facilitate mating with the calibration system, the luer 108d of an embodiment of the probe may be additionally configured to allow for a connection to and through the horizontal portion 1020a of the jig-head 1020. Embodiments of the present invention also include the use of solution-containing ampoule(s) instead of the containers such as 1012, 1014.

Once the clinician unpacks the sterilized probe, the container in which the probe has been inserted after being fabricated and as it leaves for sterilization] is hooked up to one of the three slots in the calibration jig. Similarly, the other two containers with buffer solutions are positioned in their respective slots. The proximal end of the probe is coupled (along with any temperature-control leads of the calibration jig) to a base unit running an initial resetting of signals as part of the field calibration procedure. After the resetting, the probe is removed from the travelling container to be inserted, into the first buffer-solution container, through a hollow needle that pierces the stopper 1016.

As shown in FIG. 10A, an embodiment 104 of the sensing probe is inserted in the tonometer solution 1012a by piercing of the stopper 1016 with a hollow needle 1030 through which the sensing probe 104 is protracted into the contents of the cuvette 1012. As such, the embodiment of the sensing probe is shipped from the factory. The jig-head 1020 is equipped with a sliding (for example, spring-loaded) and a rotating (m, for example, 120-degree steps, Ω) mechanisms (not shown) configured (i) to smoothly reposition the jig-head from one extreme position such as to retract, along the arrow 1024, the sensing portion 104 from its most recent position within a first cuvette such as the cuvette 1012, (ii) to incrementally rotate the jig-head 1020 about an axis 1040 so as to align the needle 1030 over an adjacent cuvette such as the cuvette 1014, and (iii) to smoothly reposition the jig-head 1020 along the arrow 1026 to bring the horizontal portion 1020a of the jig-head 1020 in close correspondence with the body 1010 and to pierce the stopper 1016 and to protract the portion 104 into the buffer solution of the second cuvette. This sequence of steps is illustrated with a sequence of FIGS. 10(A-D). Components of an embodiment of the jig may be fabricated with the use of polymeric materials (such as polycarbon or silicon, for example) and/or metallic materials (such as stainless steel). A particular choice of materials depends, in part, on the chosen method of sterilization of the probe.

The overall length of the extended jig, as shown in FIGS. 10B and 10C has to be sufficient to accommodate the clearing of the tip of the retractable needle 1030. The sliding and rotating mechanisms are configured to assure a tight seal for fluid-seepage during storage and transport of the embodiment 1000. In a specific embodiment, the jig 1000 may have an integrated calibrated temperature sensor facilitating the calibration process of temperature sensitive fluorescence-based sensors of the probe of the invention. The integrated temperature sensor may appropriately hook-up to the base unit (not shown) of the system during field calibration. In addition or alternatively, the embodiment 1000 may include a heating element (not shown) to stabilize the temperature during the calibration process.

While, as shown and discussed in reference to FIGS. 10(A-D), the embodiment 1000 includes three cuvette-like containers facilitating a two-point calibration of the sensing probe, it is understood than a larger number of containers filled with respectively corresponding pre-determined buffer solutions may be used. In this case, the sliding and rotating mechanisms of the jig should be configured to accommodate appropriate incremental placement of the needle 1030 and the sensing portion of the probe 104 into each of the cuvettes of the jig.

According to embodiments of the invention, a synthesized buffer solution, or Sensor Calibration Fluid (SCF), is biocompatible, contains electrolytes, and is characterized with a pH value within a range compatible with physiological range of the electrolytes, bicarbonate, and osmolarity values. The SCF is also configured to be tonometered with a combination of gases ($CO_2/N_2$ mixture) keeping a specific ionic strength and osmolarity. The SCF is judiciously chosen to allow for a precise identification of the blood or body fluid parameters such as, for example, pH, $O_2$, $CO_2$, $K^+$, $Na^+$, and $Cl^-$. In one embodiment of the invention, the sensor may be calibrated with a modified biocompatible Lactate Ringer's solution. Depending upon the requirement of a specific analyte calibration, various recipes or combinations of sensor calibration solution may be used. For example, such recipes and solution include the ones discussed in U.S. Pat. Nos. 5,408,999 and 6,599,746. Each of these patent documents is incorporated herein in its entirety. The latter patent discloses a calibration fluid composed of biocompatible electrolytes particularly useful for measuring blood $CO_2$. The sensor calibration solution described in this latter patent contains an anti-bacterial or anti-fungal agent to prevent any bacterial growth and increase the shelf life of the fluid for long term storage.

An integral part of chosen calibration procedure is tied up to the relative preservation of sensitivity of each sensor of the probe from the moment of its calibration at the factory calibration until its removal from the test environment. Analytically, this requires preserving a slope of the mathematical relationship governing the rate of change of the level of fluorescence in response to the change in the analyte concentration. The operation of the embodiments may be optimized as follows:

- all of the sensors may be configured equivalently, e.g., to operate by detecting the life-time fluorescence;
- all corresponding indicator matrices must be are securely accommodated and housed inside the respective chambers with robust membranes and coatings substantially eliminating the leaching of the indicator matrices from the chambers;
- low level light detection schemes should be adopted to minimize the accelerated bleaching of these indicator compounds under high levels of excitation light;
- geometry and disposition of the chambers with respect to FO-elements should be optimized as discussed in reference to FIG. 4A;
- signal referencing techniques should be adopted, that allow for the presence of light at auxiliary wavelengths, so as to minimize effects relating to instabilities in the light sources, detectors and total optical path;
- the indicator matrices have to be shielded from ambient and excessive light exposure at all times.

Even despite these optimization measures, it is hard to maintain the sensitivity of a given sensor unchanged throughout the sensor's lifetime. Embodiments of the present invention attempt to minimize unwanted influence on the process and results of sensing and monitoring produced by light-source instability, leaching, photo bleaching or sample coloration. In part, such minimization is achieved through the use of referencing methods also known as ratiometric methods of referencing the signal intensities or decay time. In one embodiment, the ratiometric method for fluorescence measurements in the frequency domain is employed, which is based on a large difference between the lifetime of the phosphorescence emission and that of the fluorescence emission generated by a dual fluorescent indicator. According to this method, a ratio of an intensity value corresponding to a long-lived emission to that corresponding to a short-lived emission is calculated by measuring the phase shift between the excitation and emission signals at two different but close optical frequencies. This approach can easily be applied to the development of a robust fluorescent optical sensor.

An alternative ratiometric method utilizes, in addition to the operational dye/indicator employed to interact with an analyte, an auxiliary internal reference indicator that is insensitive to desired analyte, but photo-decomposes at the same rate as the operational dye/indicator. When an internal reference dye is incorporated into the fiber optic sensor, the signal from the operational dye can be calibrated by comparing it with that from the reference dye indicator. Because of the decay rates of the operational and reference dyes are similar, the ratio of intensities of fluorescent emissions produced by these dyes does not substantially vary as the two dyes photo decompose upon being excited. A representative example of such radiometric method used for an optical oxygen sensor may include an operational, analyte-sensitive ruthenium-based indicator-matrix along with an auxiliary, analyte-insensitive indicator-matrix made with Oregon Green-488 Dextran dye. It will be understood by a person skilled in the art that, because the embodiments of the present invention employ a fluorescence-based time-decay approach for the analyte detection, the effects of dye leaching and bleaching do not present a serious concern. Furthermore, because most of the dyes used in the current embodiments are covalently bonded through appropriate linkers or binders, the leaching of the dye is inherently reduced as compared to the embodiments in which there is no such bonding.

An embodiment of an overall sensing system of the invention such as the embodiment of FIG. 1B has been described as including a processor controlled by instructions stored in a memory. The memory may be random access memory (RAM), read-only memory (ROM), flash memory or any other memory, or combination thereof, suitable for storing control software or other instructions and data. Those skilled in the art should readily appreciate that functions, operations, decisions, etc. of at least part of the sensing system may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Accordingly, the invention should not be viewed as being limited to the disclosed embodiment(s).

For example, in one specific embodiment at least one of the sensors (including an analyte sensor, a temperature sensor, and a pressure sensor) of the probe is based on electrical and/or mechanical elements instead of the FO-elements. For example, the temperature sensor disposed axially within the embedding body of the sensing portion of the probe may be a conventional thermocouple. Alternatively or in addition, a FO-element-based temperature sensor may be disposed not axially but in the peripheral section of the embedding body, and may employ either an in-line or an end-line chamber.

Figure 8:
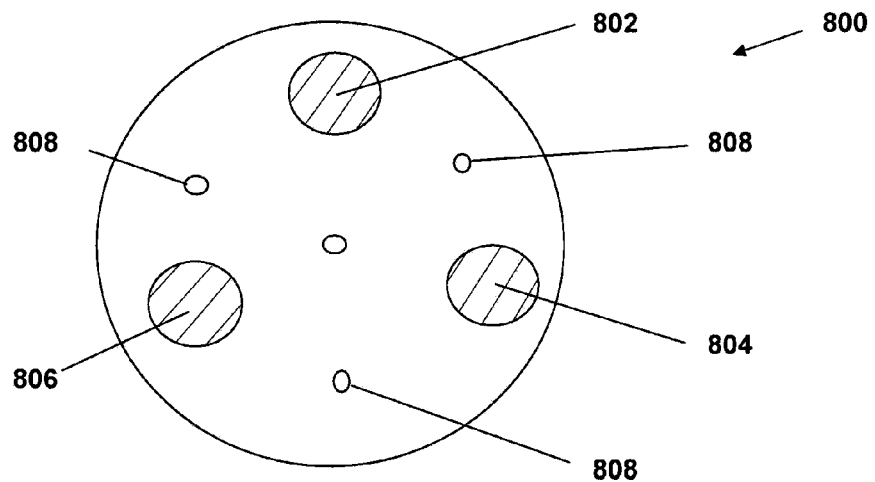
FIG. 8 shows a cross-sectional view of the sensing portion of the probe having an embedded mechanical-strength enhancing means.

In a specific embodiment, the OD of the individual FO-elements of the sensors may differ among the sensors included in the same probe. Alternatively or in addition, as shown in an embodiment 800 of FIG. 8 the sensing portion of the probe may contain, along its axis A and in addition to the sensors 802-806, at least one strand 808 made of high tensile strength material such as Kevlar™ that mechanically bolsters the sensing portion of the probe. The incorporation, on the outside surface of the sensing portion, of distance markings may facilitate the determination of how far inside the ambient medium (such as biological tissue) the sensing portion of the probe is being inserted in operation.

Figure 9:
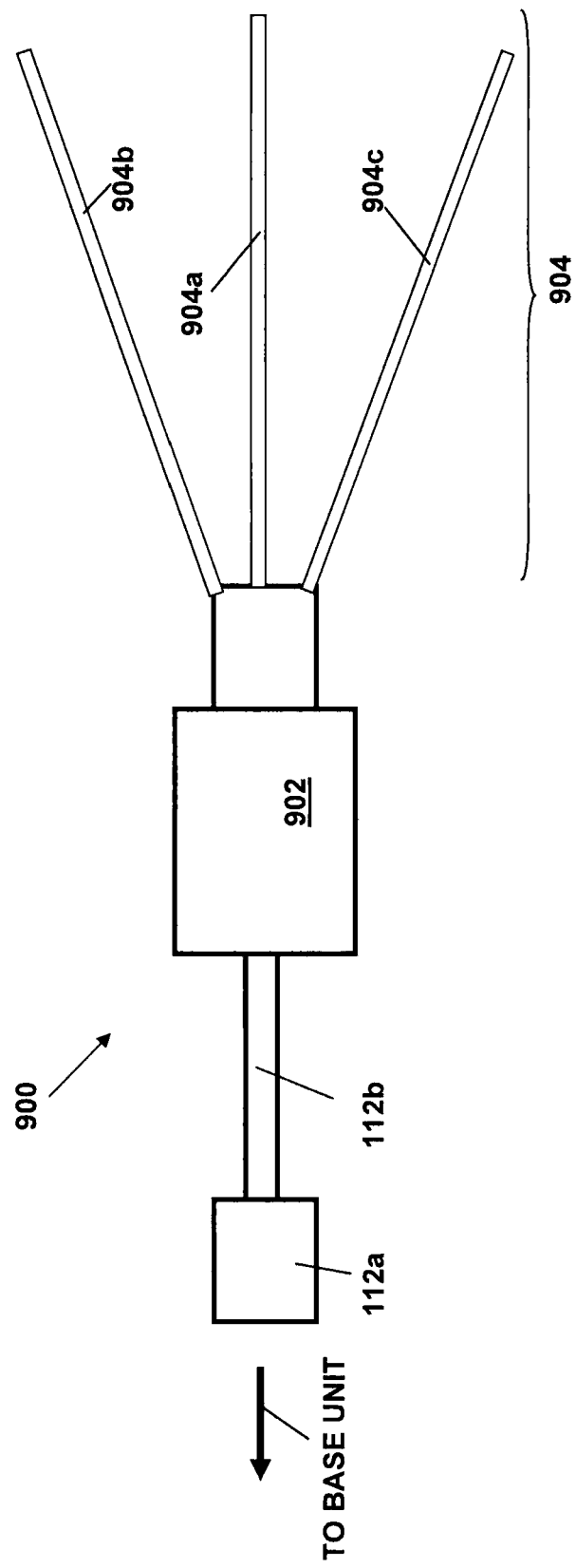
FIG. 9 illustrates a probe embodiment including multiple sensing portions.

As another example, an embodiment of the sensing portion of the probe of the invention may be configured to have a longitudinal profile that deviates from a straight line, or to have a split in its housing structure that facilitates grouping of individual sensors together based on a defined requirement. An embodiment 900 of the probe, for example, schematically shown in FIG. 9, contains an anchoring portion/Y-connecting portion denoted as 902 that provides access to a sensing portion 904 including a multiplicity of (as shown, three) sensing shafts 904a, 904b, and 904c each of which may be generally configured in a fashion described elsewhere in this application but, at the same time, be dedicated to function with respect to a particular physiological cause. For example, the sensing shaft or sub-portion 904a may contains only oxygen sensors, while the shafts 904b and 904c may be configured to perform measurements of pH and $CO_2$, respectively. In yet another configuration, all three sensing sub-portions or shafts 904(a-c) may be used to measure a single analyte (e.g., oxygen). In yet another configuration, one of the shafts may be dedicated to monitoring one type of gas (such as oxygen), while another shaft may be dedicated to monitoring two gases (e.g., oxygen and $CO_2$) and the remaining shaft may embed two types of sensors monitoring, for instance, pH and $CO_2$, respectively. It is appreciated that, in addition to these analyte sensors each of the shafts in a multiple-sensing-portion probe may contain a physical-parameter sensor (e.g., a pressure sensor or a temperature sensor).

Another modification, in reference to FIG. 4A, for example, may include a membrane patch 424 the index of refraction of which is lower than that of the indicator inside the cavity 418b, which facilitates guiding the light, generated with the use indicator in response to the analyte, back to the chamber and the FO-element 406.

In yet another modification, an indicator may be configured to include more than one dye such as first and second dyes having different operational characteristics and thus cause an embodiment of the FO-element-based sensor be configured as a two-parameter sensor. For example, in further reference to FIGS. 3(A, B), the in-line chamber 302 may be filled with an indicator-matrix containing a temperature-sensitive dye that is intermixed with an analyte-sensitive dye. In this case, each of the dyes is chosen to fluoresce at a different wavelength, thereby assuring that an optical signal corresponding to thermal calibration of the embodiment and that characterizing the presence of the analyte do not interfere. Such multi-parameter sensor provides for miniaturization of the probe design. However, when the temperature sensor employs thermocouple, it may be prudent to locate the thermocouple near the tip of the probe.

It is appreciated that a specific embodiment of the probe may be devoid of a centrally located temperature sensor, while another specific embodiment may include more than one sensor located in the central portion of the probe body.

With respect to embodiments containing a non-traumatizing tip at a distal end of the sensing portion of the probe, the tip can have any appropriate shape and be, for example, hemispherical, pyramidal, conical, or ellipsoidal, or toroidal. A toroidal configuration of the non-traumatizing tip includes a passage, through the central portion of the tip, to a surface terminating the embedding body of the probe at its distal end thus facilitating physical access to a sensor that is embedded axially. A particular shape of the tip does not change the principal of operation of an embodiment so long as the tip eases the introduction of the probe into tight orifices, pre-existing pathways and channels of the biological tissue and minimizes damage to the integrity of the tissue during any accidental or incident contact with the probe. It is appreciated that, in general, embodiments of a sensing probe of the invention may be adapted to measure parameters of any ambient medium that communicates with an indicator matrix of the probe. Also worth noting is the fact that, by virtue of having a built-in pressure sensor as described herein, an embodiment of the invention allows a user such as a clinician to simplify the conventional monitoring procedure by not using an external (to the probe) pressure-measuring equipment, thereby drastically reducing the costs associated with patient care.

Although some aspects of the method of the invention have been described with reference to a flowchart, those skilled in the art should readily appreciate that functions, operations, decisions, etc. of all or a portion of each block, or a combination of blocks, of the flowchart may be combined, separated into separate operations or performed in other orders. Moreover, while the embodiments are described in connection with various illustrative data structures, one skilled in the art will recognize that the system may be embodied using a variety of data structures. In addition, the disclosed methods and structures may be used with other materials to fabricate similar types of devices. Furthermore, disclosed aspects, or portions of these aspects, may be combined in ways not listed above.

What is claimed is:

1. A fiber-optic (FO) probe comprising:
    an elongated body having proximal and distal ends, a side surface, a peripheral portion, an axis, and an outer diameter $D_P$ at the distal end defined in a cross section in a plane perpendicular to the axis; and
    spatially discrete peripheral sensors embedded therein, each peripheral sensor defined by
        a respectively-corresponding first straight and uniform FO-element having an outer diameter $D_F$ and seamlessly cast inside a UV-cured fluid-impermeable embedding material of the distal end to extend uniformly along the axis in the peripheral portion between the proximal and distal ends and having an end-facet in said embedding material at the distal end,
        a first solitary chamber having
        a first volume, defined by one or more of first solitary chamber walls enclosing the first volume inside the embedding material,
        a width, and
        a first symmetric aperture having a corresponding first recess and providing access to the first volume through the side surface,
        said first solitary chamber disposed to terminate the respectively-corresponding first straight and uniform FO-element at the end-facet and a first chamber wall and structured such as to cause said first FO-element to transmit light from the proximal end into the first solitary chamber and from the first solitary chamber towards the proximal end while, at the same time, preventing light in the first solitary chamber from being transmitted from said chamber to a first solitary chamber of any other peripheral sensor,
        a first indicator matrix containing a first indicator material and loaded in the first solitary chamber;
    each peripheral sensor further comprising a corresponding membrane patch disposed in the corresponding recess of the symmetric aperture of the first solitary chamber and dimensioned to match a geometry of the recess to seal and prevent the contents of said first solitary chamber from leaking out of said first solitary chamber, said membrane patch being selectively permeable by an analyte corresponding to the first indicator material;
    said probe having a capacity to accommodate (i) any number of said spatially discrete peripheral sensors in a range between 1 and $Ns = \pi(D_P/(r\, D_F) - 1)$, wherein r is a ratio of the width of the first solitary chamber to $D_F$, and (ii) an additional sensor including an FO-element having an outer diameter $D_F$ and disposed axially inside the probe within a surface defined by a plurality of the peripheral sensors.

2. An FO-probe according to claim 1, wherein said first FO-element includes a single straight optical fiber devoid of a bend.

3. An FO-probe according to claim 1, wherein $D_P$ is less than 450 microns when $D_F$ is about 125 microns, r is about 1.2 and $N_S$ is 6.

4. An FO-probe according to claim 1, wherein a transverse dimension of the first solitary chamber exceeds $D_F$, wherein the first indicator material is adapted to generate a change in a level of induced fluorescent light in response to a change in an analyte concentration, the first indicator material containing at least one metal-ligand complex associated with at least one of 2,2'-bipyridine, 1,10-phenanthroline, 4,7-diphenyl-(1,10-phenanthroline), 4,7-dimethyl-(1,10-phenanthroline), 4,7-disulfonated-diphenyl-1,10-phenanthroline, 5-chloro-1,10-phenanthroline, 5-bromo-1,10-phenanthroline, a thiazole or substituted thiazoles, a platinum complex of porphyrines or substituted porphyrines, and a palladium complex of porphyrines or substituted porphyrines.

5. An FO probe according to claim 1, further comprising
    an axially-disposed sensor defined by a corresponding straight FO-element, axially disposed with respect to the probe and within the surface defined by the plurality of the peripheral sensors and having an outer diameter $D_F$, and an end-line second solitary chamber that terminates said axially-disposed FO-element at an end-facet thereof,
    wherein
    the end-line second solitary chamber has (a) a second volume defined by one or more of second solitary chamber walls enclosing the second volume inside the embedding material, and (b) a second symmetric aperture defining a plane perpendicular to the axis and having a corresponding second recess;
    both the end-line second solitary chamber and said corresponding axially-disposed FO-element are cast uniformly and seamlessly in said embedding material,
    a transverse dimension of the end-line second solitary chamber exceeds $D_F$,
    said end-line second solitary chamber is loaded with a second indicator matrix adapted to change a generation of induced fluorescent light only in response to change in ambient temperature of a test environment,
    and further comprising
    a non-permeable to fluids membrane patch disposed in the second recess and dimensioned to match a geometry of the second recess such as to seal the end-line second solitary chamber.

6. An FO-probe according to claim 5, wherein at least one wall of a first solitary chamber and at least one wall of the end-line second solitary chamber are coated with a corresponding optical thin-film coating structured to effectuate a multiple recirculation, inside said chambers, of light delivered thereto from the proximal end while preventing transmission of at least one of (i) said light delivered from the proximal end and (ii) fluorescent light originating inside at least one of said chambers from being transmitted, from inside of the at least one of said chambers, to a probe element located outside of the at least one of said chambers.

7. An FO-probe according to claim 1, wherein each peripheral sensor further comprises a second straight FO-element with an outer diameter of $D_F$ cast seamlessly and uniformly in the embedding material coaxially with the first straight FO element and having a second end-facet at the first solitary chamber wall such that the first and second straight FO-elements are spatially separated by said first solitary chamber, said second straight FO-element providing structural support for the distal end and the first solitary chamber.

8. An FO-probe according to claim 7 containing N spatially-discrete peripheral sensors, $1 \leq N \leq N_S$, wherein lengths of N second FO-elements differ from one another.

9. An FO-probe according to claim 1, further comprising a non-metallic thermally-conductive atraumatic tip cast seamlessly at the distal end.

10. An FO-probe according to claim 9, further comprising permeable to fluids hydrophobic and hydrophilic coating membranes each covering a selected cylindrical surface of the distal end such as to adjoin said atraumatic tip and to cover all apertures of the peripheral sensors.

11. An FO-probe according to claim 1, further comprising a second indicator material in said first indicator matrix, said second indicator material being insensitive to an analyte in response to which the first indicator material generates fluorescent light, said second indicator material generating a reference fluorescence light used in operation of the probe and for probe calibration.

12. A measurement system comprising an FO-probe according to claim 1, and further including
- an optical module including a light source and a light detector;
- a data-processing circuitry configured to process data representative of at least light intensity; and
- a calibration jig having an axis and including incrementally-rotating about the axis cuvettes, said jig containing a tonometered solution and enabling a calibration of the FO-probe with respect to at least two analyte-selective references.

13. A method for fabrication of a fiber-optic (FO) probe having proximal and distal ends, the method comprising:
- UV-curing an article, which includes a plurality of straight FO-elements each having an outer diameter $D_F$ and embedded into a UV-curable compound, to form a seamless and uniform body that has an axis, a side surface, the distal end, and an outer diameter $D_P$ and that encapsulates and casts simultaneously said plurality in an embedding UV-cured fluid-impermeable compound, wherein a peripheral FO-element is disposed along a cylindrical surface defined about the axis and an axial FO-element is disposed axially;
- carving out, through the side surface of the body, a portion thereof including a single longitudinal segment of the peripheral FO-element and adjacent embedding material such as to define a first solitary chamber solitarily corresponding to the peripheral FO-element in a peripheral portion of the body, said first solitary chamber being the only chamber associated with the peripheral FO-element and defining a corresponding first aperture in the side surface, a corresponding first recess associated with the first aperture, and defining (i) a gap separating first and second coaxial portions of the peripheral FO-element and (ii) end-facets of said first and second coaxial portions;
- carving out, through the distal end, an axial portion of the body including an axially located portion of the embedding material and a portion of the axial FO-element to form an end-line second chamber terminating the axial FO-element,
said second chamber defining a corresponding second aperture in the side surface and a corresponding second recess associated with the first aperture;
- sealingly closing, with a first membrane at the first recess, the first solitary chamber that has been filled with a first analyte-specific indicator matrix, the first membrane being selectively permeable by an analyte corresponding to the first analyte-specific indicator matrix, a geometry of the first membrane matching a geometry of the first recess; and
- sealingly closing, with a second membrane at the second recess, the end-line second chamber that has been filled with a temperature-sensitive indicator matrix, the second membrane being fluid-impermeable, a geometry of the second membrane matching a geometry of the second recess,
such as to form the FO-probe having a capacity to accommodate any number of spatially discrete peripheral sensors in a range between 1 and $Ns=\pi(D_P/(r\ D_F)-1)$, wherein r is a ratio of the width of the first chamber to $D_F$,
each discrete peripheral sensor defined by a corresponding first coaxial portion of a peripheral FO-element and a corresponding first solitary chamber structured such as to enable said first coaxial portion of the peripheral FO-element to transmit light between the proximal end to said first solitary chamber and from the first solitary chamber while at the same time preventing light in said first chamber from being transmitted through said first solitary chamber to a first solitary chamber of any other peripheral sensor.

14. A method according to claim 13, further comprising disposing a thin-film optical coating in each of the first and second chambers.

15. A method according to claim 13, further comprising calibrating said probe with a use of a tonometered solution with respect to at least two analyte-selective references.

16. A method according to claim 15, further comprising coating the distal end of the probe with an optically opaque hydrophilic coating and an anti-thrombogenic hydrophilic coating.

17. A method according to claim 13, further comprising:
seamlessly casting a non-traumatizing distal tip at the distal end and covering the second membrane using thermally-conductive material.

18. A method according to claim 13, further comprising:
sequentially applying and curing
- a uniform hydrophobic semi-permeable coating to a selected portion of the distal end including said distal tip, and
- a hydrophilic coating to cover the whole distal end of the probe including all apertures of the peripheral sensors.

* * * * *